United States Patent [19]

Dininno

[11] Patent Number: 5,401,735
[45] Date of Patent: Mar. 28, 1995

[54] BRIDGED BIPHENYL CARBAPENEM ANTIBACTERIAL COMPOUNDS

[75] Inventor: Frank P. Dininno, Old Bridge, N.J.

[73] Assignee: Merck & Co., Inc., Rahway, N.J.

[21] Appl. No.: 101,141

[22] Filed: Aug. 2, 1993

[51] Int. Cl.$^6$ .................. A01N 43/00; A61K 31/395; C07D 487/00
[52] U.S. Cl. ....................... 514/210; 540/302
[58] Field of Search ................. 514/210; 540/302

[56] References Cited

U.S. PATENT DOCUMENTS 4,374,849  2/1983  Christensen et al. .
5,011,832  4/1991  Dininno et al. .
5,025,006  6/1991  Dininno et al. .

FOREIGN PATENT DOCUMENTS

0416953A2  3/1991  European Pat. Off. .
0422596A3  4/1991  European Pat. Off. .
0517065A1  12/1992  European Pat. Off. .

Primary Examiner—Johann Richter
Assistant Examiner—Rebecca Cook
Attorney, Agent, or Firm—Richard C. Billups; Mark R. Daniel; Joseph F. DiPrima

[57] ABSTRACT

Carbapenems of the formula:

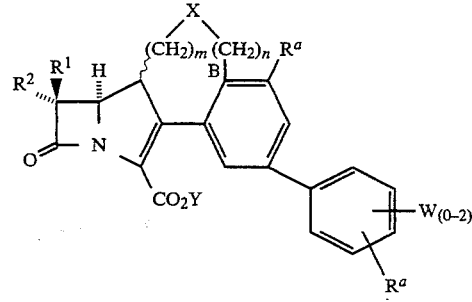

are disclosed as useful antibacterial agents.

20 Claims, No Drawings

BRIDGED BIPHENYL CARBAPENEM ANTIBACTERIAL COMPOUNDS

BACKGROUND OF THE INVENTION

The present invention relates to antibacterial agents of the carbapenem class in which the five membered ring of the carbapenem nucleus is fused to a biphenyl group which is substituted by various cationic and neutral substituents. The fused ring compounds are described in detail below.

Thienmaycin was an early carbapenem antibacterial agent having a broad spectrum; it has the following formula:

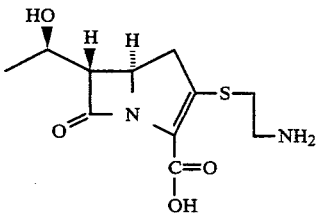

Later, N-formimidoyl thienamycin was discovered; it has the formula:

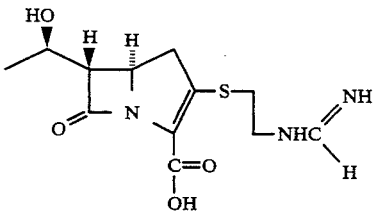

U.S. Pat. Nos. 5,011,832 and 5,025,006 relate to carbapenems of the structure shown below which exhibit antimicrobial activity against strains of methicillin resistant staphylococci (MRSA). The carbapenems described therein possess a meta-disposed biphenyl moiety attached to the C-2 position of the carbapenem ring.

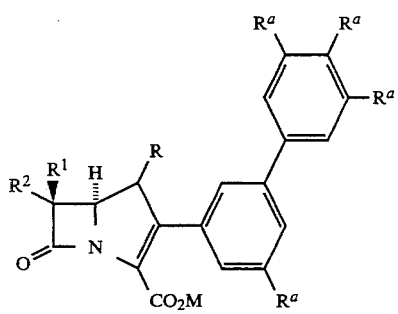

U.S. Pat. Nos. 4,374,849 and 4,374,879 issued on Feb. 22, 1983 to Christensen, et al. relate to compounds of the formula:

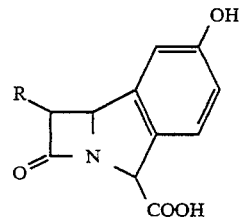

In U.S. Pat. No. 4,374,878, the R group noted above represents a hydroxy substituted ethyl group.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

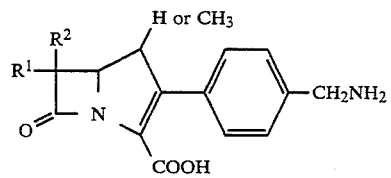

Compounds Of the formula:

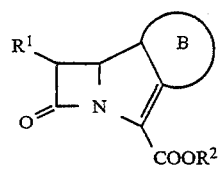

have been disclosed in EPO 422,596 A3 published on Apr. 17, 1991. European Publication No. 416 953 A3 published on Mar. 13, 1991 addresses compounds of the formula:

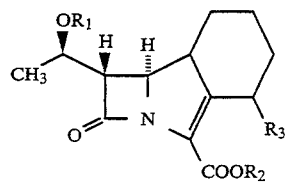

European Publication No. 517 065 A1 published on Dec. 9, 1992 addresses compounds of the formula:

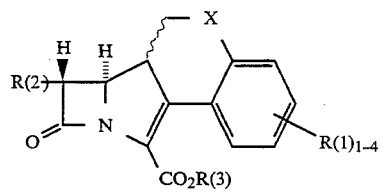

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens.

Moreover, there is an increasing need for agents. effective against such pathogens (MRSA/MRCNS) which are at the same time safe, i.e., relatively free from undesirable side effects. And, the current agent of choice, vancomycin, a glycopeptide antibacterial, is experiencing an ever increasing amount of resistance in the MRSA/MRCNS pathogens.

SUMMARY OF THE INVENTION

The present invention addresses a compound represented by formula I:

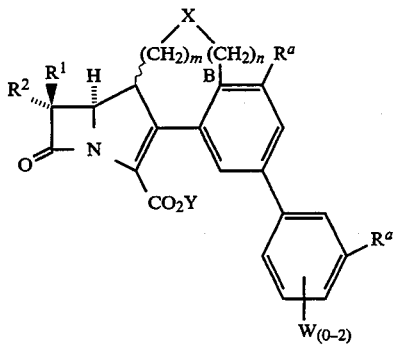

wherein:
m is an integer 0, 1, 2, 3, 4 or 5;
n is an integer 0, 1, 2, 3 or 4;
X represents (a) a bond; (b) —O—; (c) —S(O)$_x$— with x equal to 0, 1 or 2; (d) —C(O)—; (e) —NR'— with R' representing H, C$_1$ to C$_4$ alkyl, acetyl or C$_{1-4}$ alkyl substituted with R$^q$; (f) —CH=CH—; (g) —C(O)NR'—; (h) —NR'C(O)—; (i) —CO$_2$— (j) —OC(O)—; (k) —SO$_2$NR'— or (l) —NR'SO$_2$—.

The values of m, n and X are selected such that ting B constitutes a 6 to 10 membered ring.

Y represents H, a negative charge, a pharmaceutically acceptable ester, a biolabile ester, a carboxylate protecting group or a metal cation.

R$^1$ and R$^2$ independently represent H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$— or (CH$_3$)$_2$CF—.

One of the R$^a$ groups represents H or W, and the other represents one of the groups (a) through (d):

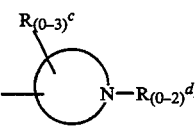

—A$_p$—NR$^{10}$R$^{11}$R$_{(0-1)}^{12}$; and (c)

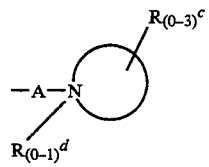

When one of the R$^a$ groups represents (a)

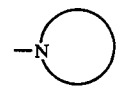

A represents —(CR$^3$R$^4$)$_r$—Q—(CR$^3$R$^4$)$_s$—wherein
r is 0–6,
s is 1–6 and
Q represents: a covalent bond, —O—, —S(O)$_x$— with x equal to 0, I or 2, —NR$^3$—, —SO$_2$NR$^3$—, —NR$^3$SO$_2$—, —C(O)NR$^3$—, —NR$^3$C(O)—, —CR$^3$=CR$^4$—, —C(O)—, —OC(O)— or —(O)CO—; with R$^3$ and R$^4$ independently representing H or C$_{1-4}$ lower alkyl,
and (CR$^3$R$^4$)$_s$— being attached to the ring nitrogen.

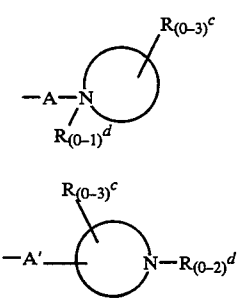

represents a 5 or 6 membered monocyclic heterocycle or an 8–10 membered bicyclic heterocycle, bonded to A through the ring nitrogen heterocycle; having a substituent group R$^d$ optionally attached to the ring nitrogen, and having 0–3 R$^c$ groups attached to other atoms of the heterocyclic group, said ring nitrogen being tertiary or quaternary by virtue of A, the ring bonds and optionally R$^d$ which may be attached, said heterocyclic group being aromatic, partially aromatic or non-aromatic, said heterocycle further containing; 0–3 additional nitrogen atoms and 0–1 oxygen or sulfur atom.

Each R$^c$ independently represents W as defined below or NR$^y$R$^z$, wherein R$^y$ and R$^z$ independently represent H, C$_1$ to C$_4$ alkyl or C$_1$ to C$_4$ alkyl substituted with R$^q$, or R$^y$ and R$^z$ are taken together to represent either a 3- to 5-membered alkylidene radical to form a ring, optionally substituted with R$^q$, or a 2- to 4-membered alkylidene radical interrupted by O or S(O)$_x$ with x equal to 0, 1 or 2, to form a ring, said alkylidene being optionally substituted with R$^q$.

R$^q$ is selected from hydroxy, methoxy, cyano, —C(O)NH$_2$, —OC(O)NH$_2$, —CHO, —OC(O)N(CH$_3$)$_2$, —SO$_2$NH$_2$. —SO$_2$N(CH$_3$)$_2$, —SOCH$_3$, —SO$_2$CH$_3$, —F, —CF$_3$, —SO$_3$M$^b$ with M$^b$ representing H or alkali metal, or —CO$_2$M$^a$, where M$^a$ is H, alkali metal, methyl or phenyl; tetrazolyl (where the point of attachment is the carbon atom of the tetrazole ring and one of the nitrogen atoms is mono-substituted by M$^a$ as defined above).

Each R$^d$ independently represents hydrogen, NH$_2$, O— or C$_1$ to C$_4$ alkyl, optionally monosubstituted with R$^q$ as defined above.

When one R$^a$ group represents (b)

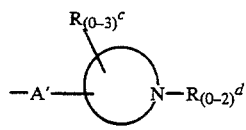

$A'$ represents $-(CR^3R^4)_{m'}-Q-(CR^3R^4)_{m'}$ with each $m'$ independently equal to 0–6, and Q, $R^3$ and $R^4$ as defined above, except that when each $m'$ is 0, Q is not a covalent bond, and $-(CR^3R^4)_{m'}$ attached to the phenyl ring.

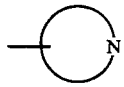

represents a 5 or 6 membered monocyclic heterocycle or an 8–10 membered bicyclic heterocycle, said heterocycle being aromatic, partially aromatic or non-aromatic, bonded to $A'$ through an atom other than the ring nitrogen, and optionally having 0–2 $R^d$ substituent groups attached to the ring nitrogen, said nitrogen in the heterocycle being tertiary or quaternary by virtue of the ring bonds and the optional $R^d$ groups which may be attached.

The heterocycle may further contain 0–1 oxygen or sulfur atom and 0–2 additional nitrogen atoms therein.

$R^c$ and $R^d$ are as defined above.

When one $R^a$ group represents (c) $-A_p-NR^{10}R^{11}R^{12}$ (0–1),

A is as defined above and p is an integer 0 or 1.

$R^{10}$, $R^{11}$ and when present, $R^{12}$, are independently H, $C_{1-4}$ alkyl or $C_{1-4}$ alkyl monosubstituted with $R^q$; or $R^{10}$, $R^{11}$ and $R^{12}$ may be taken in combination to represent a $C_4$ to $C_{10}$ alkanetriyl group, optionally substituted with up to three W groups, with W as defined below.

Where one $R^a$ group represents (d), $A'$, p, the N containing ring, $R^c$ and $R^d$ are as previously defined.

When present, each W independently represents a member selected from the group consisting of:

a) $-CF_3$;
b) a halogen atom: $-Br$, $-Cl$, $-F$ and $-I$;
c) $-OC_{1-4}$ alkyl, wherein the alkyl is optionally mono-substituted by $R^q$, where $R^q$ is as defined above;
d) $-OH$;
e) $-OC(O)R^s$, where $R^s$ is $C_{1-4}$ alkyl or phenyl, each of which is optionally mono-substituted by $R^q$ as defined above;
f) $-OC(O)N(R^y)R^z$, where $R^y$ and $R^z$ are independently H, $C_{1-4}$ alkyl, (optionally monosubstituted by $R^q$ as defined-above), or are taken together to represent a 3- to 5-membered alkylidene radical which forms a ring (optionally substituted with $R^q$ as defined above), or a 2- to 4-membered alkylidene radical interrupted by $-O-$, $-S-$, $-S(O)-$ or $-S(O)_2-$ which forms a ring, said ring being optionally mono-substituted with $R^q$ as defined above;
g) $-S(O)_n-R^s$, where $n=0–2$, and $R^s$ is defined above;
h) $-SO_2N(R^y)R^z$, where $R^y$ and $R^z$ are as defined above;
i) $N_3$
j) $-N(R^t)C(O)H$, where $R^t$ is H or $C_{1-4}$ alkyl, said alkyl group being optionally mono-substituted with $R^q$ as defined above;
k) $-N(R^t)C(O)C_{1-4}$ alkyl, wherein $R^t$ is as defined above;
l) $-N(R^t)C(O)OC_{1-4}$ alkyl, where $R^t$ is as defined above;
m) $-N(R^t)C(O)N(R^y)R^z$ where $R^t$, $R^y$ and $R^z$ are defined above;
n) $-N(R^t)SO_2R^s$, where $R^s$ and $R^t$ are as defined above;
o) $-CN$;
p) a formyl or acetalized formyl radical which is: $-C(O)H$ or $-CH(OCH_3)_2$;.
q) $-C(OCH_3)_2$ $C_1-C_4$ alkyl, where the alkyl is optionally mono-substituted by $R^q$ as defined above;
r) $-C(O)R^s$, where $R^s$ is as defined above;
s) $-(C=NOR^z)R^y$ where $R^y$ and $R^z$ are as defined above, except they may not be joined together to form a ring;
t) $-C(O)OC_{1-4}$ alkyl, where the alkyl is optionally mono-substituted by $R^q$ as defined above;
u) $-C(O)N(R^y)R^z$, where $R^y$ and $R^z$ are as defined above;
v) $-C(O)N(OR^y)R^z$, where $R^y$ and $R^z$ are as defined above, except they may not be joined together to form a ring;
w) $-C(S)N(R^y)R^z$ where $R^y$ and $R^z$ are as defined above;
x) $-COOM^a$ where $M^a$ is as defined above;
y) $-SCN$;
z) $-SCF_3$;
aa) tetrazolyl, where the point of attachment is the carbon atom of the tetrazole ring and one of the nitrogen atoms is mono-substituted by hydrogen, an alkali metal or a $C_1-C_4$ alkyl optionally substituted by $R^q$ as defined above;
ab) an anionic function selected from the group consisting of:
$P(O)(OM^a)_2$; $P(O)(OM^a)(OC_{1-4}$ alkyl); $P(O)-(OM^a)(C_{1-4}$ alkyl); $P(O)(OM^a)NR^yR^z$; $P(O)-(OM^a)NHR^x$; $SO_2M^a$; $SO_3M^a$; $SO_2NM^aC(O)N-R^yR^z$ and $SO_2NM^aCN$ wherein $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, said $R^q$, $M^a$, $R^y$ and $R^z$ being as defined above;

ac) a $C_5-C_7$ cycloalkyl group in which one of the carbon atoms in the ring is replaced by a heteroatom selected from O, S, NH, or $N(C_1-C_4$ alkyl) and in which one additional carbon may be replaced by the NH or $N(C_{1-4}$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) a $C_2-C_4$ alkenyl radical, optionally mono-substituted by one of the substituents a) to ac) above and phenyl which is optionally substituted by $R^q$ as defined above;

ae) a $C_2$–$C_4$ alkynyl radical, optionally mono-substituted by one of the substituents a) to ac) above;

af) a $C_1$–$C_4$ alkyl radical;

ag) a $C_1$–$C_4$ alkyl group mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents a) to ag) above.

Novel compositions, intermediates, processes of manufacture and methods of treatment, are also disclosed.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, W, as defined, at any available point of attachment. When the alkyl group s is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include etenyl, propenyl, butenyl and cyclohexenyl.

The term "alkynyl" refers to a hydrocarbon radical straight, branched or cyclic, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. Aryl thus contain at least one ting having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted with $R^a$ and W groups as defined below. Preferred substituted aryls include phenyl and naphthyl substituted with one or two preferred $R^a$ or W groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms, said heteroaryl group being optionally substituted with up to four $R^q$ groups.

Heteroaryl thus includes aromatic and partially aromatic groups which contain one or more heteroatoms. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyridine, pyrimidine and pyrazine and triazine.

The heteroaryl group of $R^x$ may be optionally substituted by $R^q$, as defined above, and substitution can be on one of the carbon atoms or one of the heteroatoms, although in the latter case certain substitutent choices may not be appropriate.

The term "heterocycloalkyl" refers to a cycloalkyl group (nonaromatic) in which one of the carbon atoms in the ring is replaced by a heteroatom selected from O, S, NH, or N($C_1$–$C_4$ alkyl), and in which up to three additional carbon atoms may be replaced by said hetero groups.

The term "quaternary nitrogen" refers to a tetravalent positively charged nitrogen atom including, e.g., the positively charged nitrogen in a tetraalkylammonium group (eg. tetramethylammonium, N-methylpyridinium), the positively charged s nitrogen in a protonated ammonium species (eg. trimethylhydroammonium, N-hydropyridinium), the positively charged nitrogen in an amine N-oxide (eg. N-methylmorpholine—Noxide, pyridine-N-oxide), and the positively charged nitrogen in an N-amino-ammonium group (eg. N-aminopyridinium).

The term "heteroatom" means N, S, or O, selected on an independent basis.

Alkylene (alkylidene or alkanediyl) and arylene refer to the groups noted above with divalent points of attachment. For example, phenylene is an arylene group, attached at any of the 1, 2- 1, 3- or 1, 4-positions. Examples of alkylene include —$CH_2$—, —$CH_2CH_2$—, —$CH_2CH_2CH_2$—,

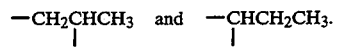

Similarly, alkanetriyl refers to an alkane-derived group with three points of attachment. Alkanetriyl groups contain from five to fifteen carbon atoms, which may be straight, branched, cyclic or multicyclic.

Aralkyl is a specie of substituted alkyl, containing up to three aryl groups substituted on a straight, branched or cycloalkyl group. The most preferred aralkyl group is benzyl.

Halogen, or "halo" refers to bromine, chlorine, fluorine and iodine.

Alkoxy refers to $C_1$–$C_4$ alkyl—O—, with the alkyl group optionally substituted with the variable $R^q$.

Carbonyloxy refers to the 5radical: —OC(O)$R^s$, where $R^s$ is $C_{1-4}$ alkyl or phenyl, each of which is optionally mono substituted by $R^q$.

Carbamoyloxy refers to the radical:—OC(O)N-($R^y$)$R^z$, where $R^y$ and $R^z$ are independently H, $C_{1-4}$ alkyl, (optionally mono-substituted by $R^q$ as defined above). Alternatively, $R^y$ and $R^z$ can be taken together to represent a 3- to 5-membered alkylidene radical which forms a ring (optionally substituted with $R^q$ as defined above), or a 2- to 4-membered alkylidene radical interrupted by —O—, —S—, —S(O)— or —S(O)$_2$— which forms a ring, said ring being optionally mono-substituted with R$^q$ as defined above.

The term "sulfur radical" refers to the group: —S(O)$_x$—R$^s$, where x is an integer of from 0 to 2, and R$^s$ is as defined above.

The term "sulfamoyl group" refers to: —SO$_2$N(R$^y$)R$^z$, where R$^y$ and R$^z$ are as defined above, representing H, alkyl or alkyl mono-substituted with R$^q$.

The term "azido" refers to the group: N$_3$.

The term "formamido" refers to the group: —N(R$^t$)-C(O)H, where R$^t$ is H or C$_{1-4}$ alkyl, said alkyl group being optionally mono-substituted with R$^q$ as defined above.

The term "alkylcarbonylamino" refers to the group: —N(R$^t$)C(O)C$_{1-4}$ alkyl, wherein R$^t$ is as defined above.

The term "alkoxycarbonylamino" refers to the group: —N(R$^t$)C(O)$^{OC}$$_{1-4}$ alkyl, where R$^t$ is as defined above.

The term "ureido" refers to the group: —N(R$^t$)-C(O)N(R$^y$)R$^z$ where R$^t$, R$^y$ and R$^z$ are defined above.

The term "sulfonamido" refers to the group: —N(R$^t$)SO$_2$R$^s$, where R$^s$ and R$^t$ are as defined above.

The terms "formyl" and "acetalized formyl radical" refer to the groups: —C(O)H or —CH(OCH$_3$)$_2$, respectively. Thus, an alkylcarbonyl radical wherein the carbonyl is acetalized is of the formula: —C(OCH$_3$)$_2$ C$_1$-C$_4$ alkyl, where the alkyl is optionally mono-substituted by R$^q$.

A "carbonyl radical" is represented by the formula: —C(O)R$^s$, where R$^s$ is as defined above.

A "hydroximinomethyl" radical in which the oxygen or carbon atom is optionally substituted by a C$_1$-C$_4$ alkyl group is represented by the formula: —(C=NOR$^z$)R$^y$ where R$^y$ and R$^z$ are as defined above, except they may not be joined together to form a ring.

An "alkoxycarbonyl" radical is represented by the formula: —C(O)OC$_{1-4}$ alkyl, where the alkyl is optionally mono-substituted by R$^q$ as defined above.

A "carbamoyl" radical is r, epresented by the formula: —C(O)N(R$^y$)R$^z$, where R$^y$ and R$^z$ are as defined.

An N-hydroxycarbamoyl Or N(C$_1$-C$_4$ alkoxy)carbamoyl radical in which the nitrogen atom may be additionally substituted by a C$_1$-C$_4$ alkyl group is represented by the formula: —C(O)N(OR$^y$)R$^z$, where R$^y$ and R$^z$ are as defined above, except they may not be joined together to form a ring.

A "thiocarbamoyl group" is represented by the structural formula: —C(S)N(R$^y$)R$^z$ where R$^y$ and R$^z$ are as defined above.

A "carboxyl group" is represented by the structural formula: —COOM$^a$ where M$^a$ is as defined above.

The term "tetrazolyl" is a heteroaryl group where the point of attachment is the carbon atom of the tetrazole ring and one of the nitrogen atoms is optionally mono-substituted by an alkali metal or a C$_1$-C$_4$ alkyl optionally substituted by R$^q$.

The term "artionic function" refers to the members of the group: phosphono [P=O(OM$^a$)$_2$]; alkylphosphono {P=O(OM$^a$)— [O(C$_1$-C$_4$ alkyl)]}; alkylphosphinyl [P=O(OM$^a$)—(C$_1$-C$_4$alkyl)]; phosphoramido [P=O(OM$^a$)N(R$^y$)R$^z$ and P=O(OM$^a$)NHR$^x$]; sulfino (SO$_2$M$^a$); sulfo (SO$_3$M$^a$); acylsulfonamides selected from: SO$_2$NM$^a$CON(R$^y$)R$^z$; and SO$_2$NM$^a$CN, where R$^x$ is phenyl or heteroaryl.

The carbapenems of the present invention contain a ring which has been designated "B". Ring B is fused between the carbapenem 5 membered ring and a phenyl ring. Ring B may be from 6 to 10 membered, optionally containing a heteroatom, such as when X represents NR', O or S(O)$_x$ with x equal to an integer, 0, 1 or 2. When X represents NR', the variable group R' may be hydrogen, acetyl, acetyl substituted with R$^q$, or C$_1$ to C$_4$ alkyl, optionally substituted with R$^q$. Ring B is also formed by the alkylene groups, (CH$_2$)$_m$ and (CH$_2$)$_n$ which may be present. In certain instances, not all values of m and n are i included in combination. When X represents a direct bond, the sum of m and n is between 2 and 6. When X represents any of the groups other than a bond, the sum of m and n is from 0 to 5. Thus, ring B constitutes a 6 to 10 membered ring.

Preferred values of m and n are such that ring B is six membered, with X preferably representing a direct bond or a heteroatom, O, S or NH.

Variables R$^3$ and R$^4$ independently represent H or lower alkyl.

One of the R$^a$ groups represents a nitrogen containing group, (a) through (d) as described above. The other R$^a$ variables represent an uncharged specie selected from H, the variables for W and NR$^y$R$^z$.

The values of R$^a$ (a) through (d) shown above can be charged or uncharged. For clarity, the positive charge has not been drawn in groups (a) through (d). When the particular nitrogen containing group is drawn as having four points of attachment, such as by attachment to the A moiety, ring bonds, R$^d$ group or groups or R$^{10}$, R$^{11}$ and R$^{12}$, the nitrogen is considered quaternary and positively charged. When the nitrogen drawn in any of groups (a) through (d) has only three points of attachment, the nitrogen is tertiary and uncharged. Tertiary nitrogen containing groups can be quatemized by standard procedures, such as the Menshutkin reaction. Both charged and uncharged nitrogen-containing compounds are included in the invention.

When one of the R$^a$ variables represents group (a), the spacer moiety —A— forms an alkylene chain, optionally interrupted with a heteroatom or functional group, —Q—. The length of A ranges from a methylene group to an alkyl chain of 12 carbon atoms in length, optionally also containing —Q— noted above. The —A— moiety bonds to the nitrogen containing ring through the N shown, and to the phenyl ring shown.

The heterocyclic group to which —A— bonds may be a heteroaryl group, a partially aromatic heterocycle or a non-aromatic heterocycle, with a substituent R$^d$ optionally bonded to the ring nitrogen. When the heterocycle is aromatic, the ring nitrogen is either uncharged or positively charged by virtue of the attachment to —A—, the ring bonds and R$^d$. R$^d$ would not be required to quaternize said ring nitrogen in (a) when the ring is aromatic. Thus, the aromatic, partially aromatic and non-aromatic forms may contain neutral or positively charge nitrogen atoms.

The heterocyclic group may also optionally contain up to three additional nitrogen atoms and up to one oxygen or sulfur atom. The heterocycle can also be substituted with up to three R$^c$ groups at any available points of attachment, either via carbon or nitrogen atoms.

When one of the R$^a$ variables represents group (b), the spacer moiety is —A— which represents an alkylene group, optionally interrupted with a heteroatom, Q. The ring structure is bonded to —A'— through an atom other than a ring nitrogen. The heterocycle can be aromatic, partially aromatic or non-aromatic. The ring nitrogen is optionally substituted with one or two groups $R^d$, as desired. When two $R^d$ groups are present on the ring nitrogen which is shown, and the structure is non-aromatic, the nitrogen is positively charged. Also, when the ring is aromatic and one $R^d$ is present on the ring nitrogen, the nitrogen is positively charged. Hence, the nitrogen may have up to two $R^d$ groups present thereon, depending on the particular configuration desired.

Also, up to three $R^c$ groups may be substituted onto the ring, at any available point of attachment.

When the variables and substituent groups are shown with bonds attached, e.g., —A—, —$R^c$, etc., this is to serve as a point of reference for application to the genetic structure, and does not indicate that double or triple bonds are intended.

When one of the $R^a$ variables represents group (c), the spacer moiety —A— represents an optional alkylene group, which in turn is optionally interrupted with Q, which may be a heteroatom, substituted mine, sulfonamide and the; like, as described above with respect to group (a). The nitrogen bound to the —A— spacer moiety is either uncharged, such as when $R^{12}$ is absent, or quaternary by virtue of the $R^{10}$, $R^{11}$ and $R^{12}$ groups present thereon and —A— attached thereto. These R groups may independently represent H, alkyl or substituted alkyl groups.

Alternatively, $R^{10}$, $R^{11}$ and $R^{12}$ may be taken together to represent a $C_4$ to $C_{10}$ alkanetriyl group, bonded to the nitrogen. Thus, the nitrogen is quaternary.

When one of the $R^a$ variables represents group (d), —A'— is as defined above for group (b). The thioether bridge is attached to the heterocyclic moiety through an atom in the ring other than the nitrogen atom which is shown.

The variable p is either 0 or 1, making the —A'— spacer moiety optional. There is a thioether bridge between the —A'— spacer moiety when present, and the heterocyclic group, or between the phenyl ring to which (d) is attached and the heterocyclic ring which is part of (d).

As noted above with respect to group (b), the nitrogen may be part of an aromatic ring, a partially aromatic heterocycle or a non-aromatic heterocycle and and may be unsubstituted, or substituted. The nitrogen may be quaternary with one or two $R^d$ groups as desired.

In each instance above, one of the $R^a$ variables represents a group selected from (a) through (d) and the other $R^a$ group represents H, $NR^yR^z$ or one of the values of W.

The bond at position one is shown as a wavy line in many instances. This indicates that the configuration of the carbon atom at position one in the carbapenem is alpha or beta, or the compound is a mixture of isomers. The preferred configuration is beta.

In the compounds of the present invention, the $R^a$ substituent may contribute to the anti-MSRA/MRCNS activity of the overall molecule, or to the other properties of the molecule.

Some $R^a$ substituents may be distinguishable from others chemically or with respect to the biological properties which they confer. In related compounds, it has been found that the charged compounds may afford greater water solubility and reduced potential for CNS side effects. Substituents which tend to confer improved water solubility on the overall Compound have been found useful, since they are contemplated to improve the pharmacokinetics of the compound involved. Although a substantial number and range of $R^a$ substituents has been described herein, all of these are contemplated to be a part of the present invention in connection with the genus of formula I.

When a group is termed "substituted", unless otherwise indicated, this means that the group contains from 1 to 3 substituents $R^q$ thereon. With respect to alkyl groups, the substituents thereon are selected from the variables specified for W. Preferred substituent groups include $C_{1-4}$ alkyl, $C_{2-6}$ alkenyl, $C_{2-6}$ alkynyl, hydroxy, $C_{1-4}$ alkoxy, aryl, heteroaryl, aralkyl, halo, cyano, nitro, carboxyl and the anionic function groups, as these terms are defined above.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as McOmie, J. (ed) *Protecting Groups in Organic Chemistry* pp. 46–119 (1973).

The preferred compounds of the invention include compounds wherein $R^1$ and $R^2$ include H and substituted lower alkyl, respectively. Preferred substituent groups include F and hydroxy. Particularly preferred are compounds where one of $R^1$ and $R^2$ is H, and the other is 1-hydroxyethyl. In the most prefered compounds $R^1$ represents H, and $R^2$ represents (R) $CH_3CH(OH)$—. The designation (R) defines the absolute configuration of the stereocenter.

The preferred compounds of the invention also include compounds where the uncharged $R^a$ variable represents H, halo, alkylthio, alkylsulfonyl or cyano.

The preferred compounds also include compounds where ring B has 6 or 7 atoms.

One preferred subgenus included in the invention relates to compounds represented by structural formula Ia:

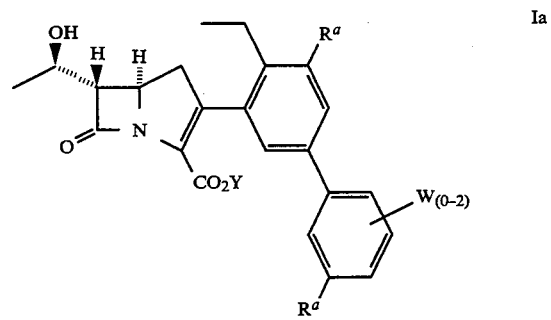

wherein
one $R^a$ represents a group (a) through (d) and the other $R^a$ represents W;
W represents any of the groups recited above;
Y represents H, a biolabile ester, a pharmaceutically acceptable cation or a negative charge.

Another preferred subgenus included in the invention relates to compounds represented by structural formula Ib:

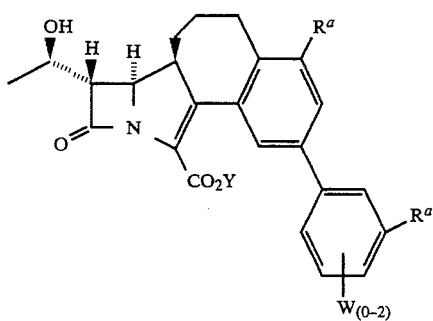

Ib

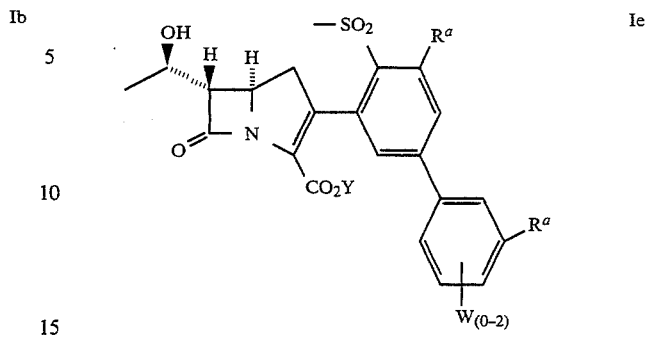

Ie wherein the values of Y, $R^a$ and W are as described above with respect to formula Ia.

Another preferred subgenus included in the invention relates to compounds represented by structural formula Ic:

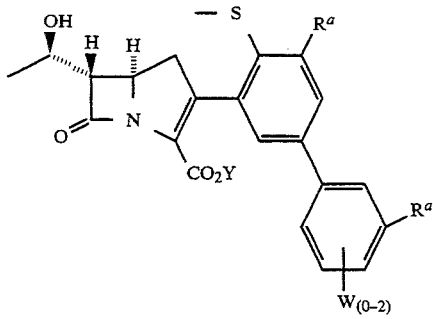

Ic wherein the values of Y, $R^a$ and W are as described above with respect to formula Ia.

Another subgenus included in the invention relates to compounds represented by structural formula Id:

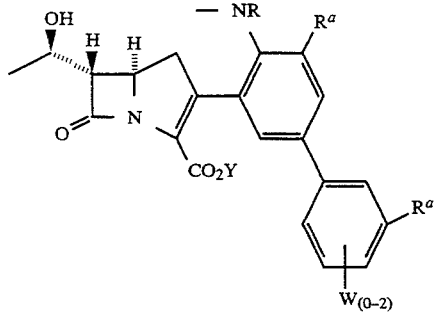

Id wherein the values of Y, $R^a$ and W are as described above with respect to formula Ia.

Another subgenus included in the invention relates to compounds represented by structural formula Ie:

wherein the values of Y, $R^a$ and W are as described above with respect to formula Ia.

Another subgenus included in the invention relates to compounds represented by structural formula If:

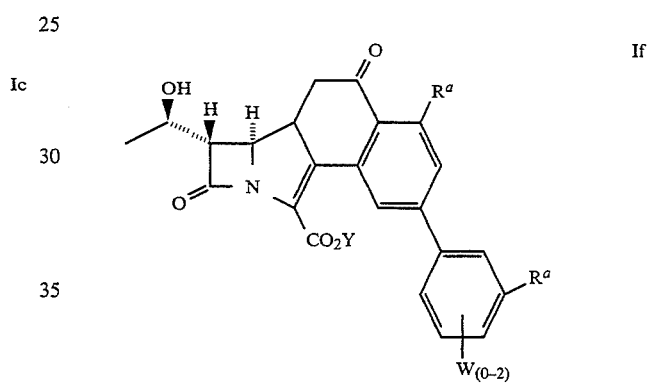

If wherein the values of Y, $R^a$ and W are as described above with respect to formula Ia.

Another subgenus included in the invention relates to compounds represented by structural formula Ig:

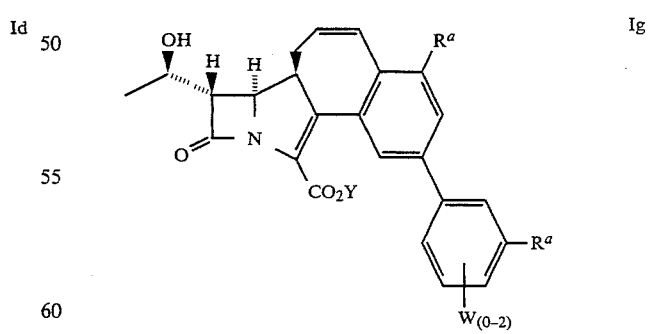

Ig wherein the values of Y, $R^a$ and W are as described above with respect to formula Ia.

Another subgenus included in the invention relates to compounds represented by structural formula Ih:

Ih

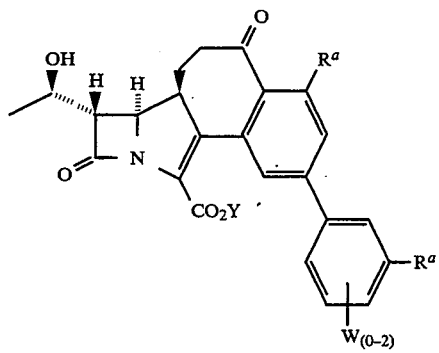

wherein the values of Y, $R^a$ and W are as described above with respect to formula Ia.

Preferred values of $R^a$ type (a) include the following structures:

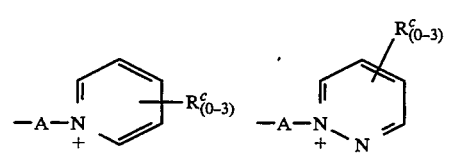

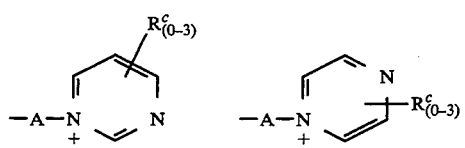

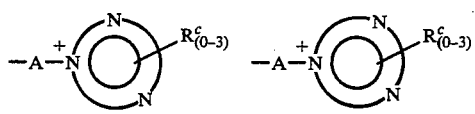

where the ring contains 3 carbon atoms | where the ring contains two carbon atoms

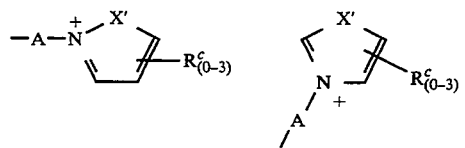

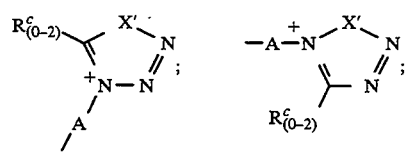

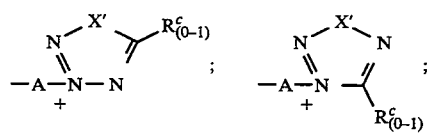

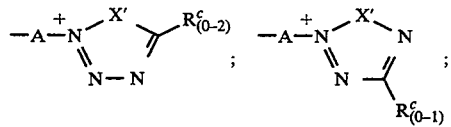

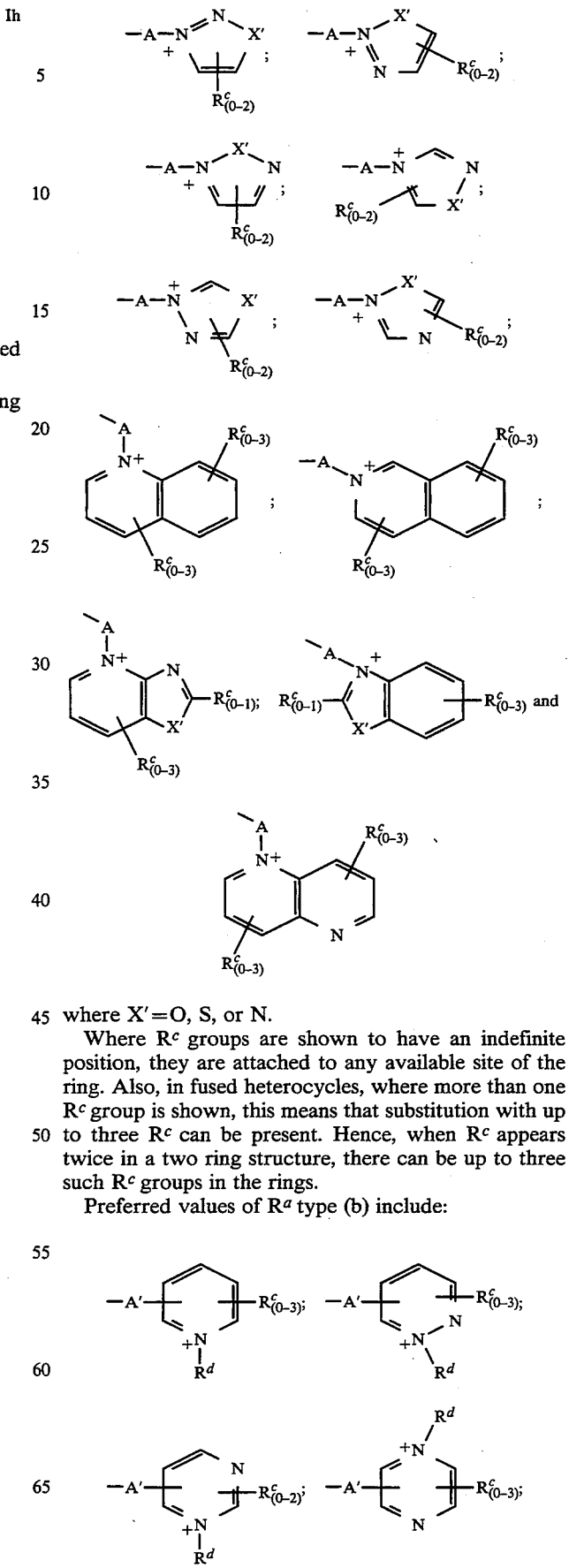

where X'=O, S, or N.

Where $R^c$ groups are shown to have an indefinite position, they are attached to any available site of the ring. Also, in fused heterocycles, where more than one $R^c$ group is shown, this means that substitution with up to three $R^c$ can be present. Hence, when $R^c$ appears twice in a two ring structure, there can be up to three such $R^c$ groups in the rings.

Preferred values of $R^a$ type (b) include:

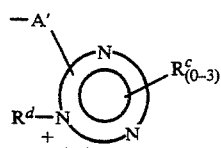 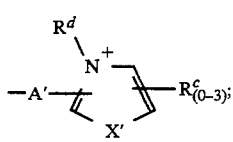

where the ring contains
three carbon atoms;

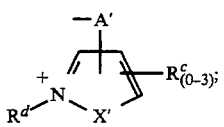

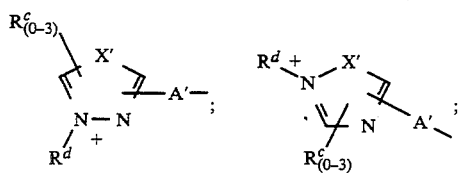

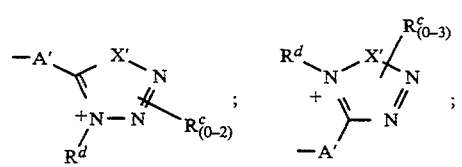

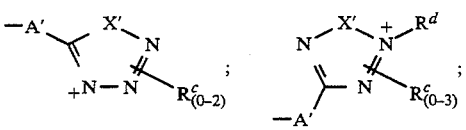

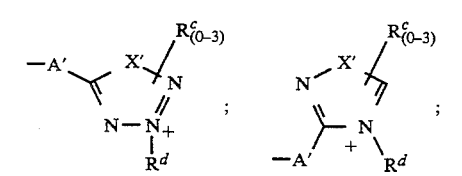

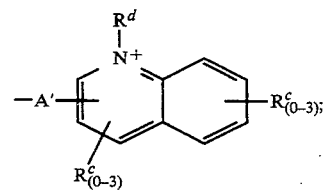

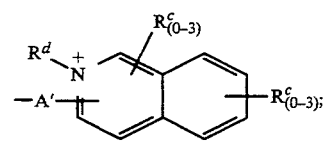

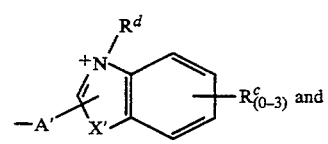

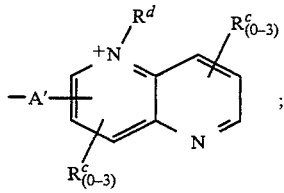

where X′=O or S.

For structures of type (b), where R$^c$ and/or A′ are shown to have indefinite positions, they are independently attached to any available atom of the ring.

Preferred R$^a$ type (c) substituents include:

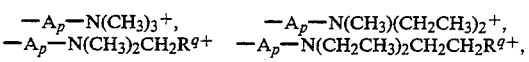

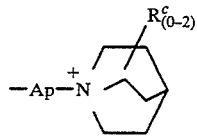

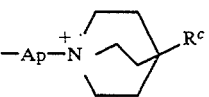

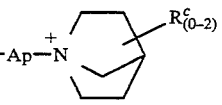

Preferred R$^a$ type (d) values include:

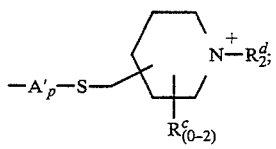

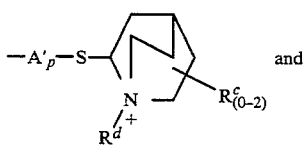

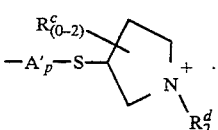

The preferred compounds are zwitterionic by virtue of a positively charged nitrogen atom in group (a)–(d) and a negatively charged carboxylate group (Y represents a negative charge).

The scope of R$^c$ includes those groups suitable for attachment to ring carbon and nitrogen atoms. Persons skilled in the art will readily recognize that a wide range of organic substituents are suitably used as R$^c$. Persons skilled in the art will also recognize that some substituents, such as the —NR$^y$R$^z$ substituents, are useful carbon substitution but not equally useful for nitrogen substitution.

Preferred $R^c$ groups attached to ring carbon atoms are —$NH_2$, —$SCH_3$, —$SOCH_3$, —$CH_2OH$, —$(CH_2)_2OH$, —$OCH_3$, —$COOM^b$, —$CH_2COOM^b$, —$CH_2CH_2COOM^b$, —$CH_2SOCH_3$, —$CH_2SCH_3$, —$SO_3M^b$, —$CH_2SO_3M^b$, —$CH_2CH_2SO_3M^b$, —Br, —Cl, —F, —I, —$CH_3$, —$CH_2CH_3$, —$CH_2CONH_2$ and —$CH_2CON(C_1-C_4 alkyl)_2$ where $M^b$ is defined above.

Preferred $R^c$ groups attached to ring nitrogen atoms are —$CH_2OH$, —$(CH_2)_2OH$, —$CH_2COOM^b$, —$CH_2CH_2COOM^b$, —$CH_2SOCH_3$, —$CH_2SCH_3$, —$CH_2SO_3M^b$, —$CH_2CH_2SO_3M^b$, —$CH_3$, —$CH_2CH_3$, —$CH_2CONH_2$ and —$CH_2CON(C_1-C_4 alkyl)_2$ where $M^b$ is defined above.

Preferred A spacer moieties include —$CH_2$—, —$CH_2$—$CH_2$—, —$CH_2$—$CH_2$—$CH_2$—, —$CH_2$—$CH_2$—$CH_2$—$CH_2$—, —$OCH_2CH_2$—, —$SOCH_2$—, —$SO_2CH_2$—, —$SCH_2CH_2$—, —$SOCH_2CH_2$—, —$SO_2CH_2CH_2$—, —$NHCH_2CH_2$—, —$N(CH_3)CH_2CH_2$—, —$CH_2N(CH_3)CH_2CH_2$—, —$CONHCH_2CH_2$—, —$SO_2NHCH_2CH_2$—, —$COCH_2$—, —$CH=CHCH_2$— and —$CH_2OCH_2CH_2$—. Preferably, where Q is O, S, NH or $N(C_{1-4}alkyl)$, then r plus s is 2-6.

Preferred —A'— groups include the preferred groups listed for A above. Further, A' may represent —O—, —S—, —NH—, —$SO_2$—, —$SO_2NH$—, —CONH—, —CH=CH—, —$CH_2S$—, —$CH_2NH$—, —$CONHCH_2$— or —$SO_2NHCH_2$—.

In X, when X represents $S(O)_x$, the preferred value of x is zero, and when X represents NR', the preferred value of R' is H.

In $R^a$ and W, when these variables represent alkoxy substituted with $R^q$, the preferred $R^q$ values are —OH, —$OCH_3$, —$CF_3$ and —$CO_2M^1$. In —$COOM^a$, the preferred values of $M^a$ are H and methyl.

When $R^a$ or W represents —$OC(O)R^s$, the preferred $R^s$ values are $C_{1-4}$ alkyl and substituted $C_{1-4}$ alkyl.

When $R^a$ or W represents —$OC(O)NR^yR^z$, the preferred $R^y$ and $R^z$ values are H, lower alkyl and $C_{4-5}$ alkylidene.

When $R^a$ or W represents —$S(O)_x$— $R^s$, x preferably is zero, and $R^s$ is preferably alkyl.

When $R^a$ or W represents —$SO_2NR^yR^z$, $R^y$ and $R^z$ preferably represent H, lower alkyl or are taken together to represent a $C_{4-5}$ alkylidene group.

When $R^a$ or W represents —$N(R^t)C(O)H$, —$N(R^t)C(O)C$— $C_{1-4}$ alkyl or substituted alkyl, —$N(R^t)C(O)OC_{1-4}$ alkyl or substituted alkyl, —$N(R^t)C(O)NR^yR^z$ or —$NR^tSO_2R^s$, the preferred $R^t$ groups are H and $C_{1-4}$ lower alkyl.

When $R^a$ or W represents a $C_{5-7}$ cycloalkyl group where one carbon is replaced with a heteroatom, —NH—, O, or —$S(O)_x$—, the preferred heteroatom is nitrogen, either —NH— or —$N(C_{1-4}alkyl)$—.

When $R^a$ or W represents an alkenyl group, the preferred alkenyl group is allyl, —$CH_2CH=CH_2$.

Among the more preferred $R^a$ groups are $C_{1-4}$ alkyl mono-substituted with hydroxy, such as, hydroxymethyl; formyl; carbamoyl, such as, —$CONH_2$; cyano; halo, such as iodo; $C_1$ to $C_4$ alkylthio, such as methylthio and its dioxides, such as —$SO_2CH_3$; and mono substituted $C_2$ to $C_4$ alkylthio, such as hydroxyethylthio, —$SCH_2CH_2OH$.

In addition to the above, examples of the more preferred $R^a$ and W groups include:

—$OCH_3$
—$OCH_2CH_2OH$     —$OCH_2CO_2Me$

| -continued | |
|---|---|
| —F | —$CF_3$ |
| —Br | —Cl |
| —OH | —I |
| —$OCONH_2$ | —$OCOCH_3$ |
| —$SOCH_3$ | —$SCH_3$ |
| —$SCH_2CH_2OH$ | —$SO_2CH_3$ |
| —$SO_2NH_2$ | —$SOCH_2CH_2OH$ |
| —NHCHO | —$SO_2N(CH_3)_2$ |
| —$NHCO_2CH_3$ | —$NHCOCH_3$ |
| —CN | —$NHSO_2CH_3$ |
| —$COCH_3$ | —CHO |
| —CH=NOH | —$COCH_2OH$ |
| —CH=$NOCH_2CO_2Me$ | —CH=$NOCH_3$ |
| —$SO_2CH_2CH_2OH$ | —CH=$NOCMe_2CO_2Me$ |
| —CH=$NOCMe_2CO_2Me$ | —$CO_2CH_2CH_2OH$ |
| —$CONH_2$ | —$CONHCH_3$ |
| —$CON(CH_3)_2$ | —$CONHCH_2CN$ |
| —$CONHCH_2CONH_2$ | —$CONHCH_2CO_2Me$ |
| —CONHOH | —$CONHCH_3$ |

Listed below are the more preferred compounds of the invention. The following numbering system applies:

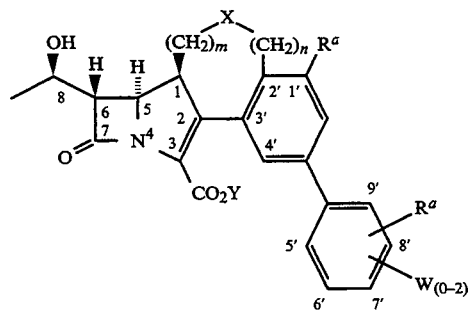

wherein the representation of $R^a$ includes attachment in either aromatic ring, at positions 1', 6', 7' or 8'. The most preferred compounds of the invention include the following:

Compounds where m and in represent 1; m represents 1 and n represents zero; and m represents 2 and n represents zero;

X represents a bond, —O—, —S—, —$SO_2$—, —C(O)—, —NH—, —CH=CH— and —C(O)NH—;

Y represents a negative charge and $R^a$ is selected from: —CH=CH— and —C(O)NH—;

Y represents a negative charge and $R^a$ is selected from:

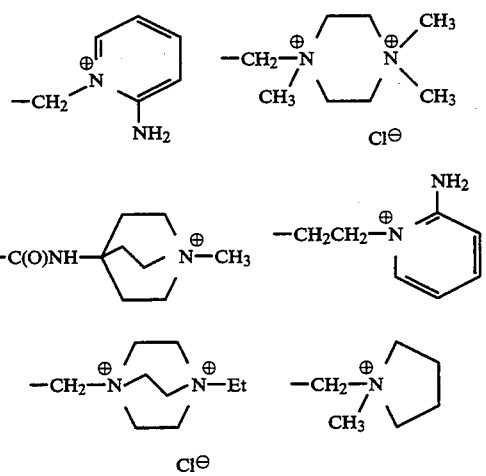

-continued

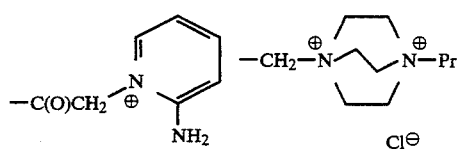

Pr = propyl
Et = ethyl

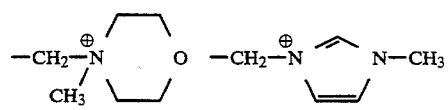

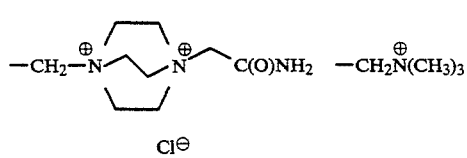

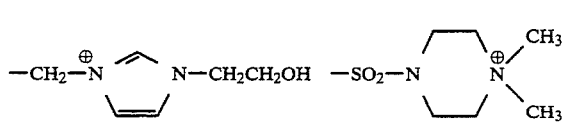

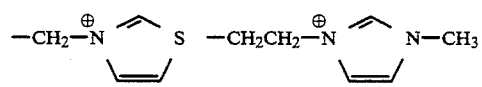

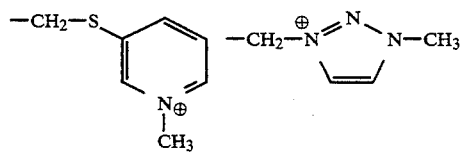

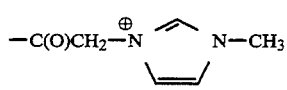

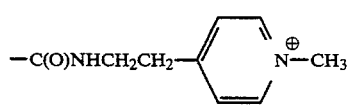

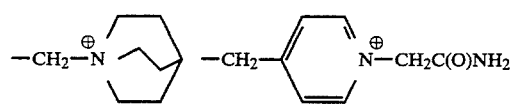

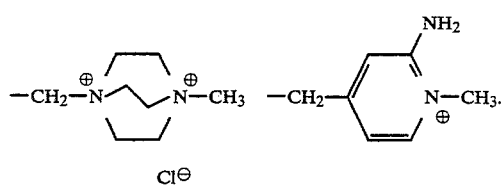

The compounds of the invention can be synthesized in accordance with the following general schemes and examples.

GENERAL SYNTHESIS OF SUBSTITUTED-PHENYL-SUBSTITUTED TETRALONES

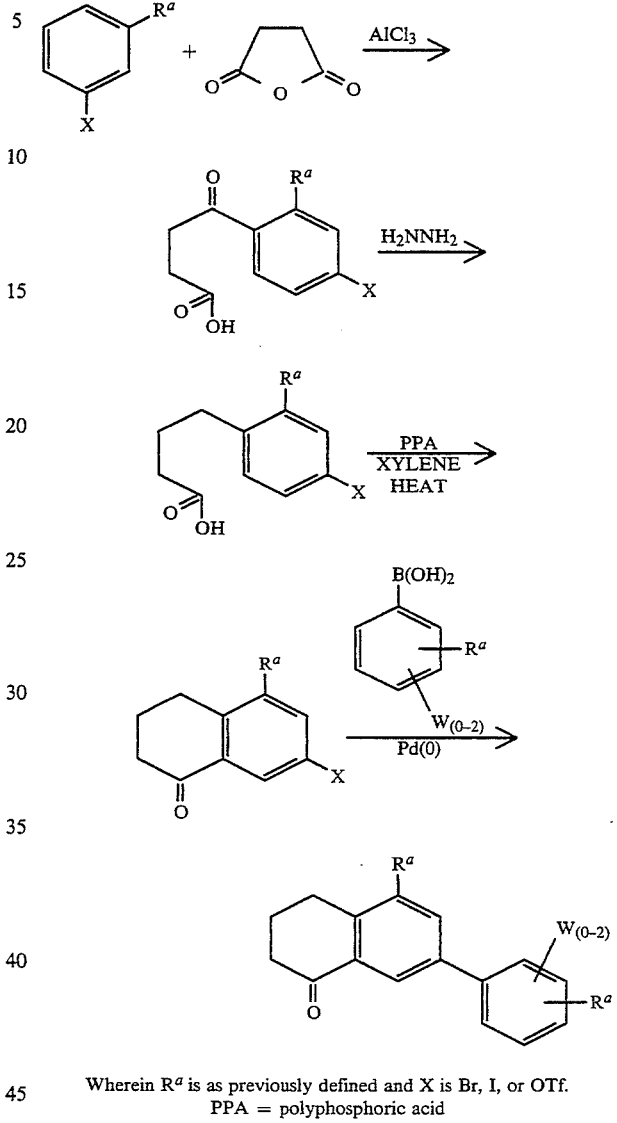

Wherein $R^a$ is as previously defined and X is Br, I, or OTf.
PPA = polyphosphoric acid

SYNTHESIS OF SUBSTITUTED-PHENYL-4-OXO-4-H-BENZOPYRAN AND THIOPYRAN

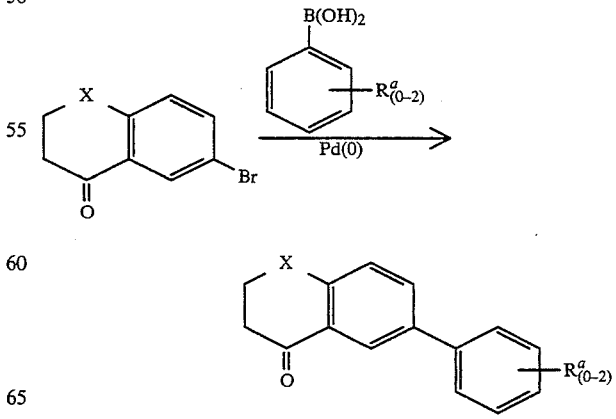

Wherein $R^a$ and X = O, S

SCHEME I
SYNTHESIS OF QUADRACYCLIC-CARBAPENEMS
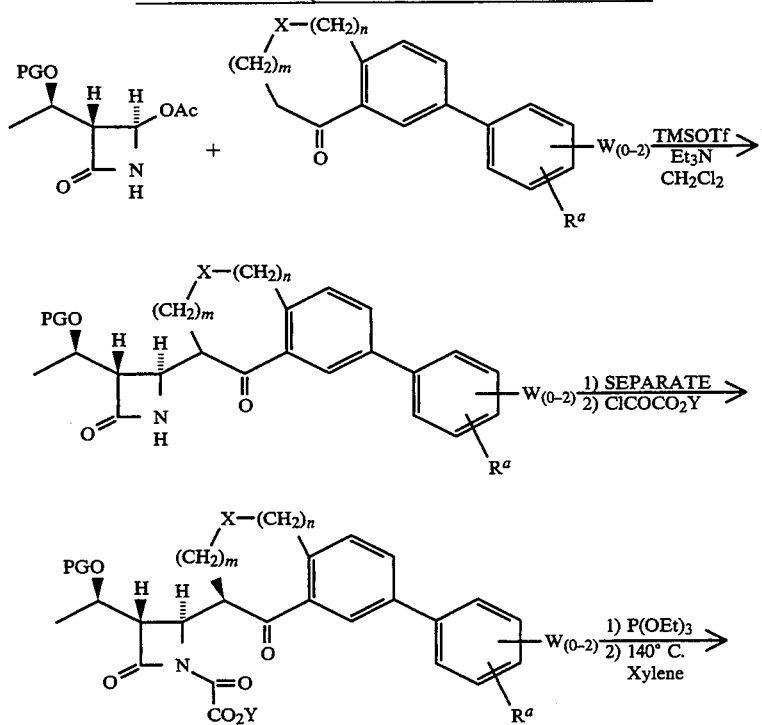
PG = Protecting Group    TMSOTF = trimethylsilyltriflate
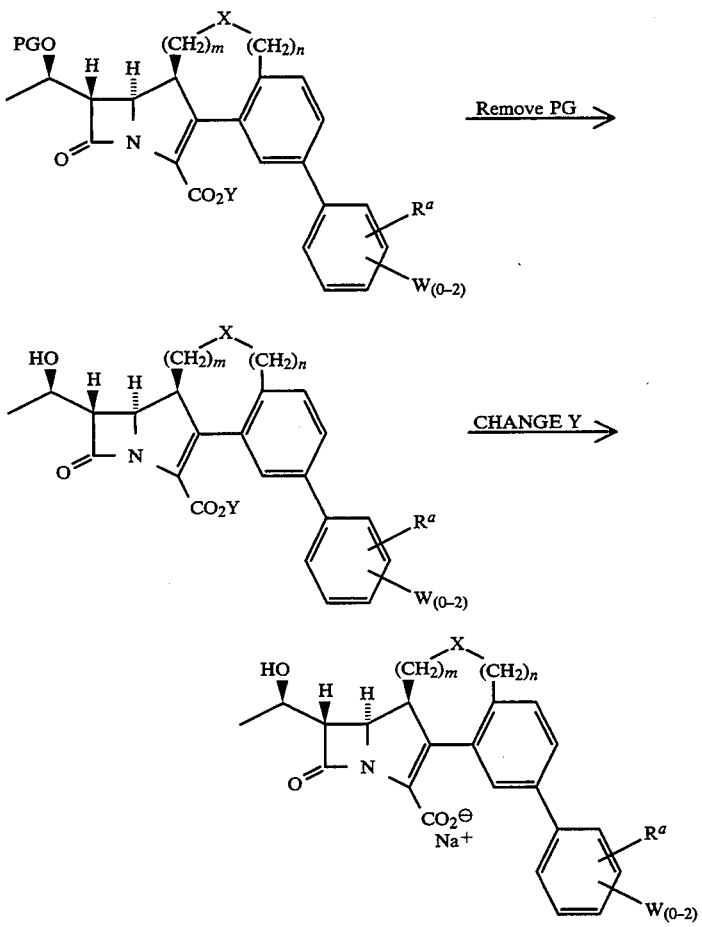

-continued
SCHEME I
SYNTHESIS OF QUADRACYCLIC-CARBAPENEMS
Wherein PG, X, R$^a$, and Y are as previously defined.
SCHEME II
SYNTHESIS OF QUADRACYCLIC-CARBAPENEMS
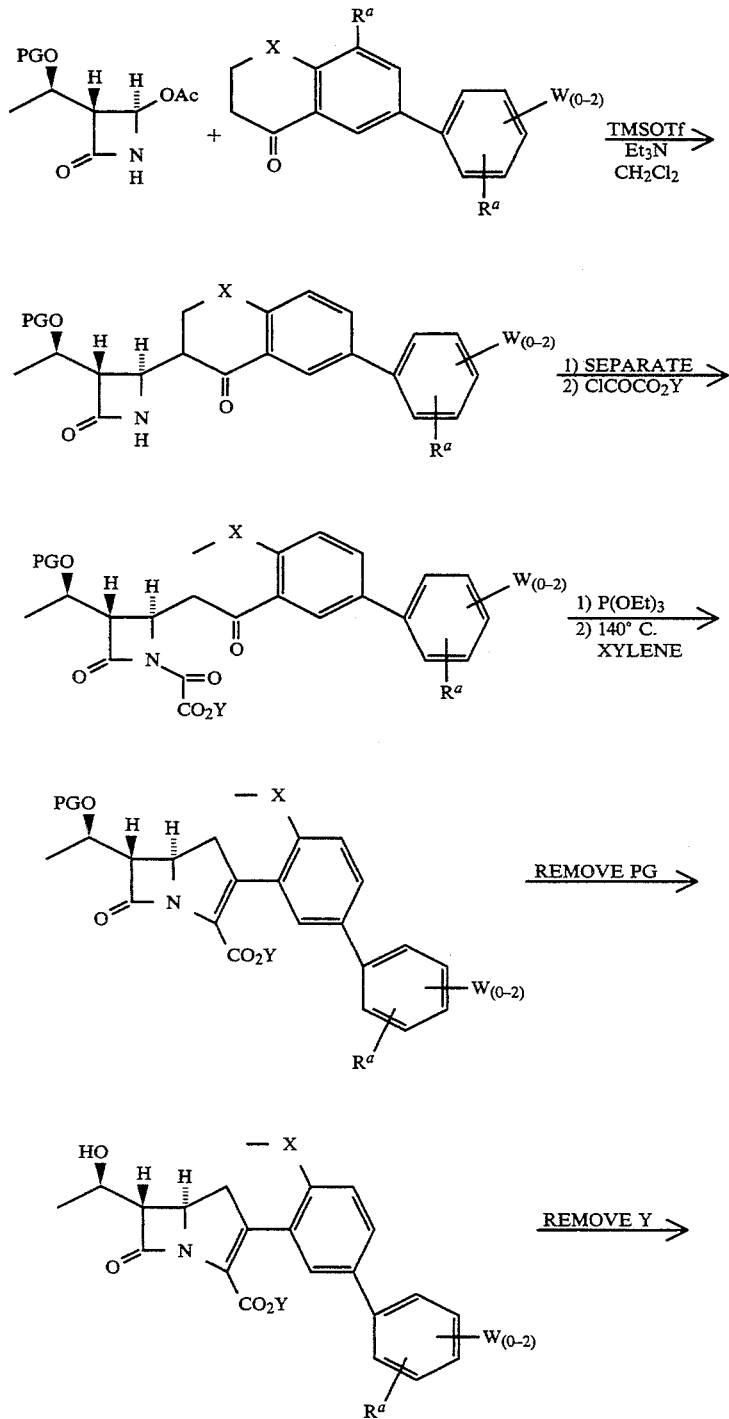

SCHEME II
SYNTHESIS OF QUADRACYCLIC-CARBAPENEMS
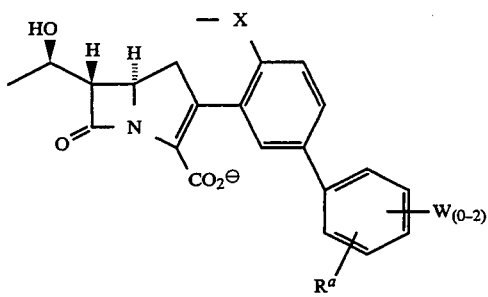
Wherein PG, X, W, $R^a$, and Y are as previously defined.
SCHEME III.
SYNTHESIS OF QUADRACYCLIC-CARBAPENEMS
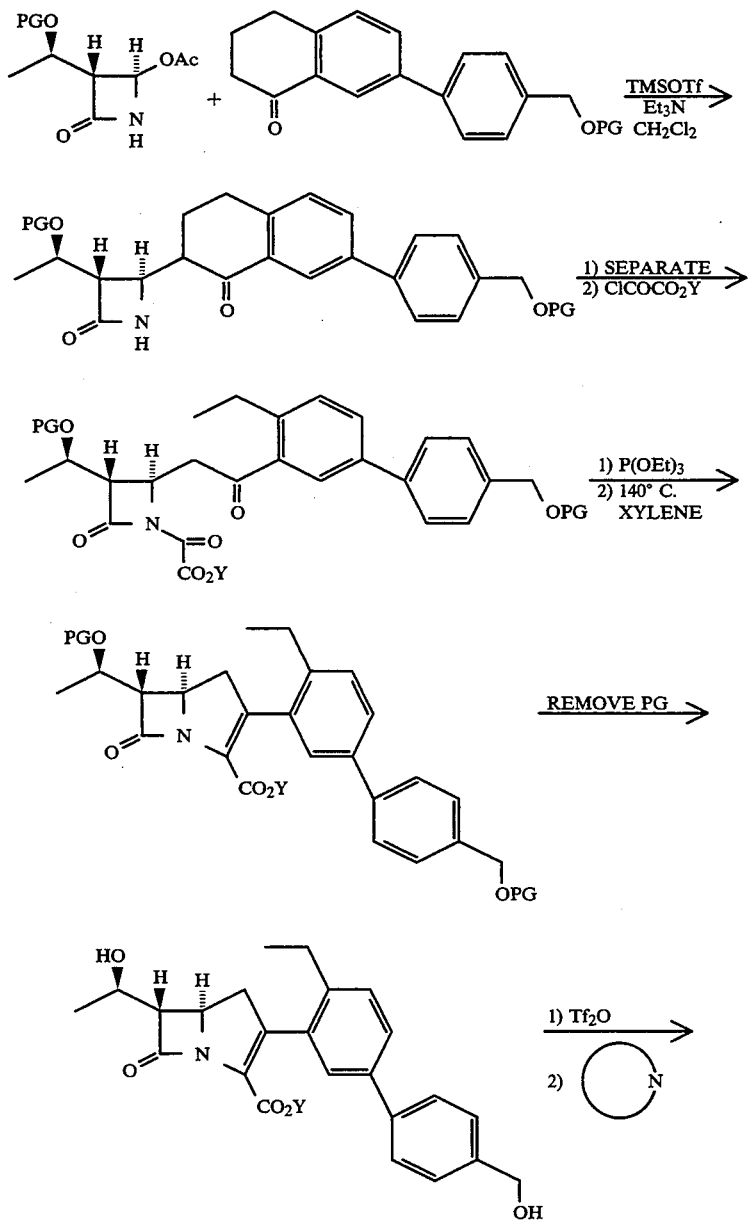

SCHEME III.
SYNTHESIS OF QUADRACYCLIC-CARBAPENEMS
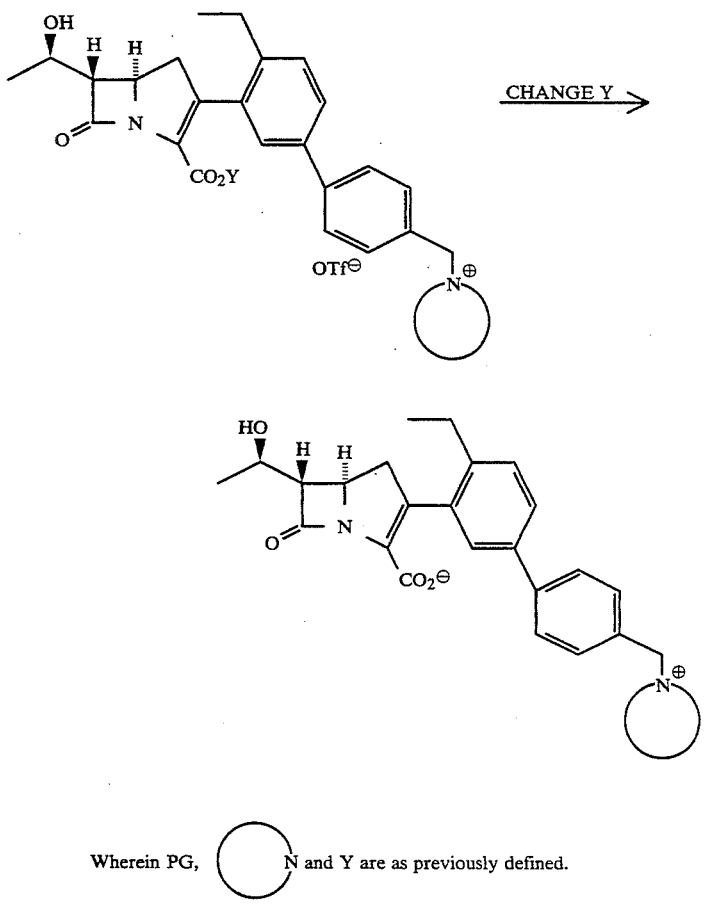
Wherein PG, ⬭N and Y are as previously defined.
Tf₂O = triflic anhydride
SCHEME IV.
SYNTHESIS OF QUADRACYCLIC-CARBAPENEMS
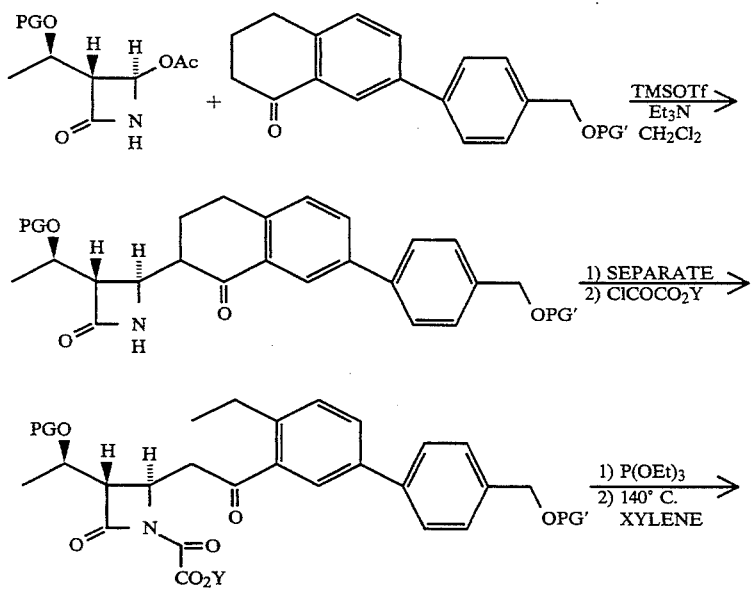

SCHEME IV.
SYNTHESIS OF QUADRACYCLIC-CARBAPENEMS
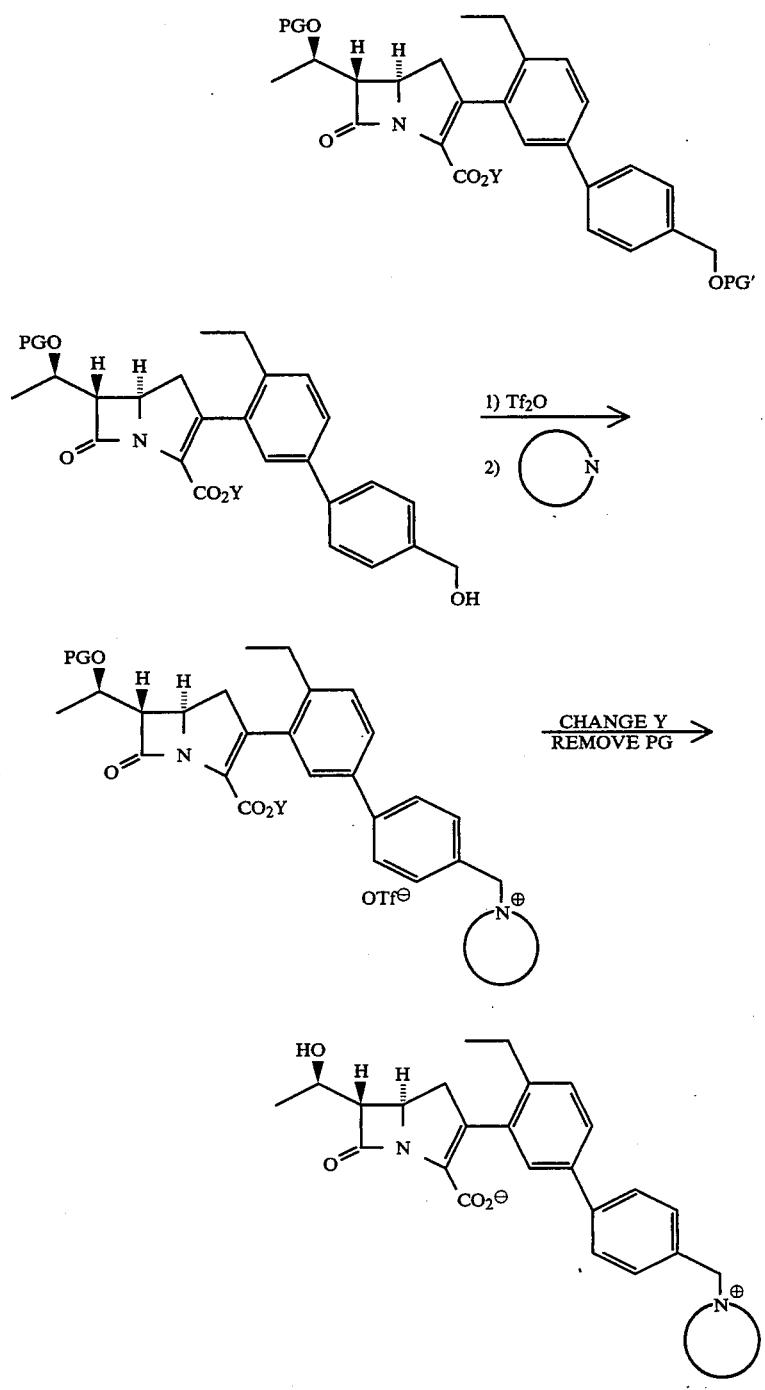
Wherein PG, PG', and Y are as previously defined.
SCHEME V.
SYNTHESIS OF QUADRACYCLIC-CARBAPENEMS
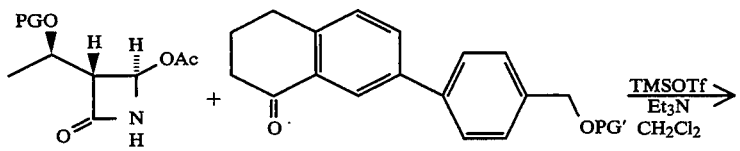

-continued
SCHEME V.
SYNTHESIS OF QUADRACYCLIC-CARBAPENEMS
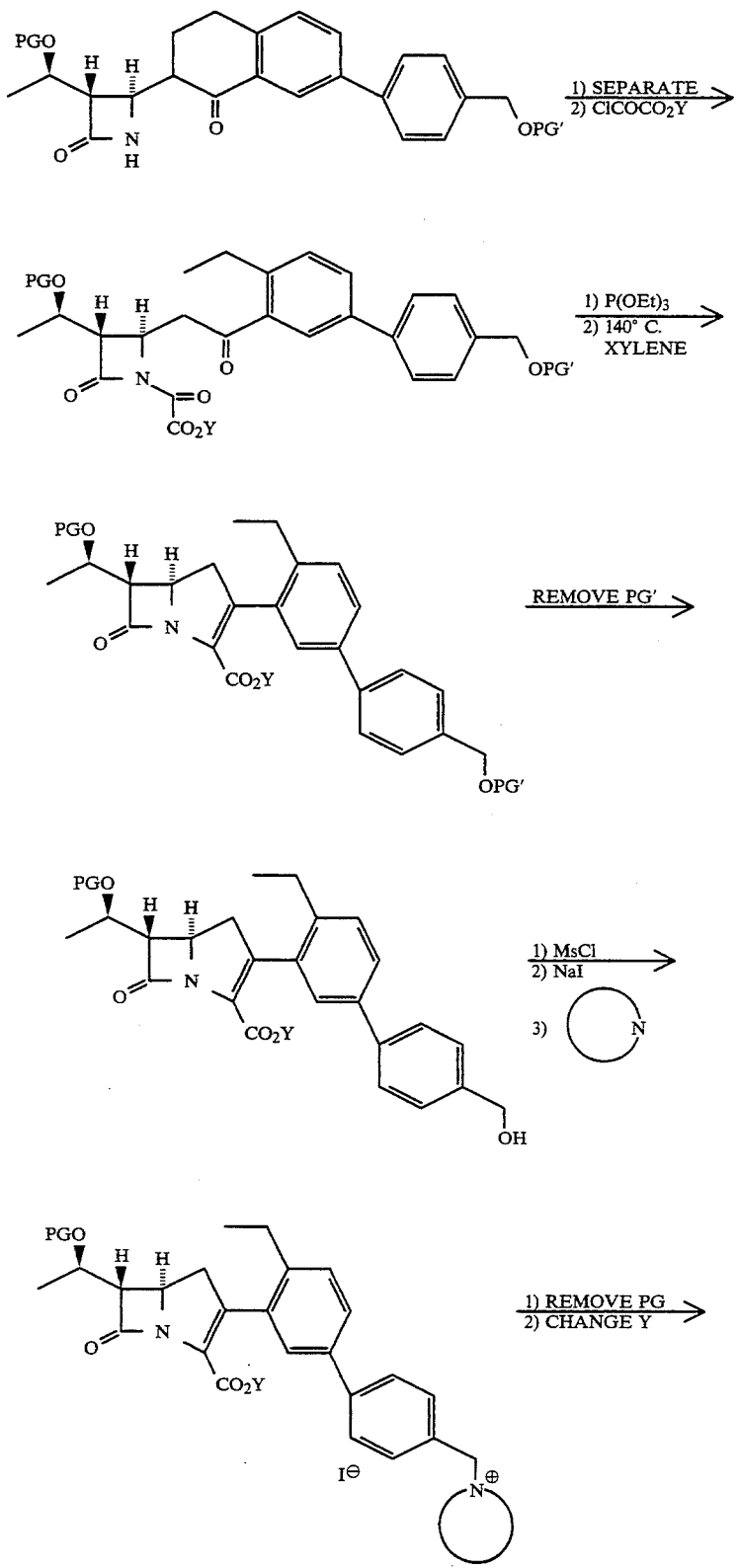

SCHEME V.
SYNTHESIS OF QUADRACYCLIC-CARBAPENEMS

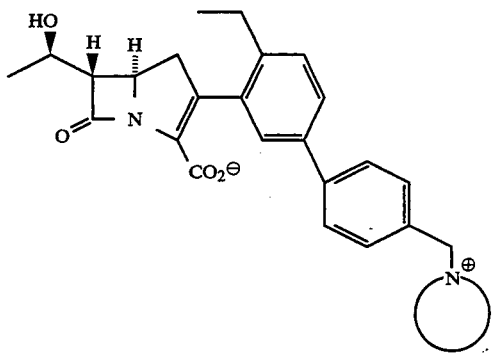

Wherein PG, PG', and Y are as previously defined.

The syntheses of compounds I are outlined in Schemes I, II, and III, which depict strategies that progress from the most general to the more specific. Basically, the skeletal arrangement of these molecules can be assembled in three key stages. Initially, the known, appropriately substituted acetoxyazetidinone is reacted with a cycloalkanonylaromatic compound in the presence of a tertiary amine base such as triethylamine, diisopropylethylamine, pyridine or the like, and a silylating agent such as trimethylsilyltrifluoromethanesulfonate, in a solvent such as dichloromethane, acetonitrile or the like, at a temperature of from −23° C. to ambient temperatures, for from 1 to 24 hours, in an inert atmosphere. The reaction is such that the cycloalkanone is converted in situ to its corresponding silylenolether derivative, which in turn reacts with the activated form of the azetidinone, brought about by the the interaction of the acetoxyazetidinone with a relatively small percentage of the trimethylsilyltrifluoromethanesulfonate, to form a carbon-carbon bond from C-4 of the azetidinone to the alpha carbon of the cycloalkanone. The latter constitutes a new stereocenter in the adduct, and the ratio of the resulting diastereomers is typically almost equal. The isomers maybe separated by standard techniques and processed individually. Alteratively, the silylenolether derivative of the cycloalkanone may be produced in a separate operation and then brought into interaction with the acetoxyazetidinone derivative and an activating agent or Lewis acid such as trimethylsilyltrifluoromethanesulfonate, zinc chloride, zinc iodide, boron-trifluoride etherate, stannous chloride, tin triflate, titanium trichloride, aluminium chloride or the like, in aprotic solvents such as dichloromethane, acetonitrile, benzene, THF, hexane or the like. In this way, the stereochemical outcome of the reaction maybe altered to produce a predominance of one isomer or the other.

The second key stage is the conversion of the newly formed azetidinone to the corresponding Wittig intermediate via the "oxalimide process". This conversion is accomplished in two steps and begins with the reaction of the azetidinone and the known, appropriately protected chlorooxalylester reagent, in the presence of a suitable base such as pyridine, triethylamine or the like, in an inert solvent such a dichloromethane, toluene, or the like, from a temperature of from −23° C. to ambient temperatures, for from a few minutes to several hours. Typically the oxalimide which is rapidly formed is isolated by conventional techniques and may be similarly purified or, more conveniently, used directly in the second step of the process. Here the oxalimide is heated with a large excess (10–20 equivalents) of an alkoxyphosphine reagent such as triethoxyphosphine, diethoxymethylphosphine, or the like, in an inert solvent such as benzene, toluene, xylene, or the like, at a temperature of from 50° C. to 120° C. for from a few minutes to several hours. The resulting alkoxyphosphorane intermediate is typically not isolated due to its hydrolytic lability, but instead can be used in situ in the final stage of the synthesis.

The last key stage involves the thermal cyclization of the alkoxyphosphorane intermediate in an inert solvent such as benzene, toluene, xylene or the like, at refluxing temperatures, in an inert atmosphere of nitrogen or helium, in the presence of a trace of hydroquinone, for from an hour to five days.

At this juncture, the remaining number of steps to complete the synthesis of the compounds I of the invention may vary. In cases where a hydroxyl group is present in the group at C-6 of the carbapenem nucleus or on the aromatic C-2 appendage, and it is covered with a protecting group (PG), the protecting group(s) maybe removed by established methods, which are discussed further below. In this instance, and in examples requiring no further chemistry at this stage, the carboxyl protecting group is analogously removed to affect the formation of I. Examples of this procedure are outlined in Schemes I and II.

On the other hand, prior to the removal of the carboxyl protecting group, additional chemistry ! maybe performed which allows for the introduction of functionality consistent with the scope of the invention. For example, Scheme III depicts a chemoselective activation of a benzylic type hydroxyl group and subsequent displacement with nucleophiles, described herein, to generate penultimate intermediates to the desired I. This process is further detailed below.

Other examples of chemical transformations which can be implemented at the carbapenem stage of the synthesis provide for certain definitions of X, including, e.g.; oxidation at a sulfur atom to provide either the corresponding sulfoxide or sulfone.

The starting materials for the initial stage of the foregoing sequence are either known in the art or can be readily prepared by established methods. In this regard the following references may be applicable:

5-phenyl-1-tetralone: K. Itoh, etal, *Chem. Pharm. Bull.*, 32, 130(1984); 6-phenyl-1-tetralone: K. Itoh, etal, ibid.; M. S. Newman and H. V. Zahm, *J. Amer. Chem. Soc.*, 65, 1097(1943); N. L. Allinger and E. S. Jones, *J. Org. Chem.*, 27, 70(1962); 7-phenyl-1-tetralone: R. Buckle, etal, *J. Medicinal Chem.*, 20, 1059(1977); M. Weizmann, etal, *Chemistry and Industry*, 402(1940); A. R. Katritzky and C. M. Marson, *J. Chem. Soc., Perkin II*, 1455(1983); 7—bromo-1-tetralone: L. F. Fieser and A. M. Seligman, *J. Amer. Chem. Soc.*, 60, 170(1938); 6—amino-1-tetralone: N. L. Allinger and E. S. Jones, supra.

For syntheses involving the Suzuki reaction, see A. Suzuki, et al, *Syn. Comm.*, 11, 513(1981); and related chemistry: Wiley, P. F., *J. Amer. Chem. Soc.*, 73, 4205(1951); Flemming, W., etal, *Chem. Ber.*, 58, 1612(1925); N. Miyaura, T. Yanagi, and A. Suzuki, *Syn. Comm.*, 11, 513(1981); V. Snieckus, etal, *J. Org. Chem.*, 56, 3763(1991); V. N. Kalinin, *Synthesis*, 413, (1992); V. Snieckus, etal, *Tet. Letters*, 29, 5459(1988); V. Snieckus and M. A. Siddiqui, ibid, 5463(1988).

For coupling to a known azetidinone to the side chain using Lewis acid catalysis, see, e.g., A. G. M. Barrett & P. Quayle, *J. Chem. Soc. Chem. Comm.* 1076(1981); Reider, P. J., et al. *Tet. Let.* 23, 2293 (1982); Hirai, K. et al. *Heterocycles* 17, 201 (1982); R. P. Attrill, A. G. M. Barrett, P. Quayle, J. Van der Westhuizen & M. J. Betts, *J. Org. Chem.* 49, 1679 (1984)

The synthesis, substitution and elaboration of dibenzofurans and dibenzothiophenes has been well reviewed in the literature: M. V. Sargent & P. O. Stransky, *Adv. Heterocycl. Chem.* 35, 1–81 (1984); W. E. Parham *Heterocyclyl. Comp.*, 2, 123 (1951); R. Livingstone in *Rodd's Chemistry of Carbon Compounds*, 2d ed. Vol. IV Part A, *Heterocyclic Compounds*, 194–202 (1973); F. M. Dean and M. V. Sargent in *Comprehensive Heterocyclic Chemistry*, Vol. 4, Part 3,599 (1979); J. Ashby & C. C. Cook, *Adv. Heterocycl. Comp.* 2, 164 (1951); R. Livingstone in *Rodd's Chemistry of Carbon Compounds*, 2d ed., Vol. IV, Pan A, *Heterocyclic Compounds*, 300–305 (1973); S. Rajappa in *Comprehensive Heterocyclic Chemistry*, Vol. 4, Part 3, 741 (1979); E. Campaigne, ibid., 863 (1979).

In Scheme V, the hydroxymethyl precursor substituent may be elaborated into the desired substituent group by convening the hydroxyl into an active leaving group such as an iodide (giving —A—I), followed by reaction with a desired nitrogen containing aromatic compound. More particularly, two alternative procedures may be utilized to produce a leaving group on the moiety —A— and subsequently to replace such a leaving group with the desired substituent.

For the first procedure, the hydroxyl group of —A—OH may be convened to a methanesulfonate group by treating with methanesulfonyl chloride (MsCl) in the presence of triethylamine. A suitable solvent, e.g., dichloromethane, is employed and the reaction is carded out at reduced temperatures. In turn, the methanesulfonate intermediate may be convened to the reactive iodide derivative by treatment with sodium iodide in a suitable solvent, e.g., acetone, at reduced or ambient temperatures. Alternatively, the hydroxyl group may be directly convened into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the desired substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desirable.

In a second procedure, the hydroxyl group of —A—OH may be converted into the reactive trifluoromethanesulfonate (triflate) group (Scheme IV). However, such an activating group cannot be isolated by conventional techniques but may be formed and used in situ. Thus, treatment of the hydroxyl group with a slight excess of trifluoromethanesulfonic (triflic) anhydride in the presence of a hindered, non-nucleophilic base such as 2,6-lutidine, 2,4,6-collidine, or 2,6-di-tert-butyl-4-methyl-pyridine in a suitable solvent, such as dichloromethane, at reduced temperatures provides for the generation of the triflate activating group. Introduction of the desired group is then accomplished by reacting the above triflate in situ with the desired nitrogen containing compound at reduced temperature.

In certain cases it is possible and desirable to use the reactive nitrogen containing compound! as the base for the formation of the triflate activating group. In this case, treatment of the hydroxyl group with triflic anhydride in the presence of at least two equivalents of the reacting nitrogen compound under the conditions described above provides the desired N-containing substituent.

Where the N ring contains: substitution with a substituent $R^c$, the most facile method of providing such a substituent is to employ as the reactant in the preparation methods described above a nitrogen containing compound which already has the desired $R^c$ substituent in place. Such substituted compounds are readily available starting materials or may be prepared in a straightforward manner using known literature methods.

In one suggested synthesis, the hydroxyl may be convened to a reactive leaving group such as iodo, which is then reacted in a nucleophilic displacement reaction with a nitrogen containing aromatic compound which has a nucleophilic side-chain substituent such as $CH_2SH$ or $CH_2NH_2$. In this displacement reaction, it is the side-chain substituent that is the reacting nucleophile and not the aromatic ring nitrogen. Suitable substrates for this reaction include 2-(mercaptomethyl)-pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine.

A second suggested synthesis starting from a precursor A'—OH (e.g. hydroxymethyl) consists of oxidation of the alcohol functionally to an aidehyde followedify Wittig-type olefination with an appropriate nitrogen-containing aromatic substituted reagent. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aidehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane and thiazolylmethylenetriphenylphosphorane. Depending on the particular $R^a$ group desired, many other synthesis schemes may be employed, as would be apparent to an organic chemist skilled in the art.

Compounds where $R^a$ represents type (c) may be prepared in an analogous manner to that described for type (a) substituents, except that the nitrogen containing compound employed in the displacement reaction is an aliphatic amine (i.e. $NR^yR^z$). In cases where the amino group is directly bonded to the ring nucleus (i.e. $-A_pNR^yR^z$ where p=O) the amine! is most conveniently attached to the ring structure prior to its incorporation into the carbapenem system.

If such an amine is primary or secondary, it may require protection with a suitable amine protecting group during the steps employed to attach the ring structure to the carbapenem. Tertiary amines typically require no protection.

Compounds where $R^a$ represents (d) may be prepared by reacting the compound $A'_p$—S—L (Leaving Group) with an N containing ring, prior to connection to the carbapenem. In the preparation methods described above, the carboxyl group at the 3-position and the hydroxyl group at the 8-position of the preferred carbapenem remain blocked by protecting groups until the final product is prepared. Deblocking may be carded out in a conventional manner. For compounds ! prepared according to the Flow Sheets, below deprotection may be carried out first by desilylation using tetrabutylammonium fluoride and acetic acid and second by deallylation using a palladium catalyzed reaction in a solution containing potassium 2-ethylhexanoate or, alternatively, another suitable nucleophile such as pyrrolidine. Alternatively, deprotection may be conducted sequentially. Thus, the protected precusor compound is exposed initially to aqueous acidic conditions, acetic acid or dilute HCl or the like, in an organic solvent such as tetrahydrofuran at 0° C. to 50° C. for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ or buffer such as sodium phosphate and 10% Pd/C followed by hydrogenation provides for the removal of the p-nitrobenzyl protecting group and the formation of the final compound of Formula I.

The carbapenem compounds of the present invention are useful per se and in their pharmaceutically acceptable salt and ester forms in the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carders.

Thus, the present invention is also concerned with pharmaceutical compositions and methods of treating bacterial infections utilizing as an active ingredient the novel carbapenem compounds.

The pharmaceutically acceptable salts referred to above may take the form —COOY. The Y may be an alkali metal cation such as sodium or potassium. Other pharmaceutically acceptable cations for Y may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalare, pamoate, pectinate, persulfate, 3-phenylpropionate, picrate, pivalate, propionate, succinate, tartrate, thiocyanate, tosylate, and undecanoate.

The pharmaceutically acceptable esters of the present invention are such as would be readily iapparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. The esters which are hydrolizable under physiological conditions are also referred to as "biolabile esters". Many biolabile esters have oral activity, protecting the drug from excessive acid degradation upon oral administration.

Some of the groups which Y represents form biolabile esters with the carboxylate to which Y is attached. Biolabile exters are biologically hydrolizable, and many are suitable for oral administration, due to good absorption through the stomach or intenstinal mucosa, resistance to gastric acid degradation and other factors. Examples of biolabile esters include compounds in which Y represents an alkoxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. All of these groups can be substituted in the alkyl or aryl portions thereof with acyl or halo groups. The following Y species are preferred as biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

Some of the novel carbapenem compounds of the present invention take the form COOY, where Y is a readily removable carboxyl protecting group. Such conventional groups consist of known groups which are used to protectively block the carboxyl group during the synthesis procedures described therein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation. Examples of such ester protecting groups include benzhydryl, p-nitrobenzyl, 2-naphthylmethyl, allyl, benzyl, trichloroethyl, silyl such as trimethylsilyl or trimethylsilylethyl, phenacyl, p-methoxybenzyl, acetonyl, o-nitrobenzyl, p-methoxyphenyl, 4-pyridylmethyl, and t-butyl.

Likewise, the hydroxy group at position 8 can be protected as appropriate to facilitate the syntheses described herein.

The compounds of the present invention are valuable antibacterial agents active against various Gram-positive and to a lesser extent Gram-negative bacteria, and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in compositions in concentrations ranging from about 0.01 to about 100 parts of antibiotic per million parts of solution in order to destroy or inhibit the growth of harmful bacteria on medical and dental equipment and as bactericides in industrial applications, for example in water based paints and in the white water of paper mills to inhibit the growth of harmful bacteria.

Many of compounds of the present invention are biologically active against MRSA/MRCNS. This is demonstrated below using the following biological activity protocol.

In vitro antibacterial activity determined in accordance with the protocol set forth below is predictive of in vivo activity, when the compounds are administered to a mammal infected with a susceptible bacterial organism.

Minimum inhibitory concentrations for different compounds may be calculated using the procedures set forth in Lorian, V. (ed.) *Antibiotics in Laboratory Medicine* (3rd ed.) pages 30–35 if desired. However, by comparing disc sensitivities to a known compound, e.g., imipenem, this calculation is not required to recognize MRSA/MRCNS activity.

Assay Used to Test the Activities of Carbapenems Against Methicillin-Resistant Staphylococci The assay is an antibiotic disc-diffusion assay modeled after the method described by Bauer and Kirby, et al., with the following modifications and clarifications:

Agar: This assay employs an agar depth of 2 mm instead of 4 mm.

Zone Readings: The inner, completely clear zone is measured.

Culture Storage: Frozen Vials of strains are stored at $-80°$ C. Working slants are prepared from frozen vials and are used for 1 month to 6 weeks. For methicillia-resistant2 strains the slant medium is Muleller Hinton Agar; for control strains the slant medium is Brain Heart Infusion Agar. After inoculation from frozen vials, methicillin-resistant slant cultures are incubated at 28° C. until good growth is achieved (approximately 20 hours); slants of control strains are incubated at 37° C. for 16–18 hours.

Preparation of Control Inocula for Assay: Pipet 2 ml Brain Heart Infusion Broth (BHIB) into a sterile, plastic 17×100 mm tube. Use a sterile cotton tipped applicator to pick up a very small amount of culture from the slant land twirl it in the BHIB to achieve a light but visible inoculum (approximately $1 \times 10^6$–$10^7$ cfu/ml). Incubate at 37° C. and 220 rpm for 17–18 hours.

Preparation of Methicillin-Resistant Inocula for Assay: For methicillin-resistant strains, inoculate 0.5 ml of BHIB heavily (to achieve approximately $1 \times 10^8$–$10^9$ cfu/ml) from the slant culture by using a sterile cotton tipped applicator. With the applicator spread approximately 0.1 ml of the suspension onto the surface of a 15×100 mm petri plate containing 10 ml Mueller Hinton Agar. Incubate the plate at 30° C. for approximately 18 hours.

Inoculum Adjustment: The 17–18 hour control Staphylococci cultures are diluted 100× in phosphate-buffered saline (PBS).

Methicillin-resistant Staphylococci: With a cotton tipped applicator, swab enough growth off the grown plates into 1 ml BHIB to achieve a visual concentration of approximately $1 \times 10^9$ cfu/ml. Mix vigorously and dilute in PBS so that dilutions appear visually to be slightly more concentrated than the 100× diluted control cultures. Measure % transmission (% T) at 660 nm in a Spectronic 20 or other spectrophotometer. Add measured quantities of PBS to dilutions to achieve % T @ 1% above or below the % T measurement for the control cultures. Make sterile dilutions using the same proprotions.

Plate Incubation Following Plate Inoculation and Disc Placement: Incubate control plates for 18 hours at 37° C. Incubate methicillin-resistant Staphylococci plates for 18 hours at 30° C.

Using the tests described above, the compounds of the invention are active against MRSA, as demonstrated in the following table. Imipenem is the standard, and is assigned a relative activity level of 1. The other compounds have the activity which is indicated relative to that of imipenem.

TABLE

| Compound | Relative Activity |
| --- | --- |
| Imipenem (MIC = 46 mg/mL | 1.0 |

TABLE-continued

| Compound | Relative Activity |
|---|---|
| [structure] | 1.9 |
| [structure] | 1.3 |
| [structure] | 2.6 |
| [structure] | 18.8 |
| [structure] | 20.0 |

Based upon the foregoing, the compounds of the present invention exhibits activity against MRSA (Strain MB #5180) which is unexpected.

The compounds of this invention may be used in a variety of pharmaceutical preparations. They may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain formulating agents. Alternatively, the active ingredient may be in powder (lyophillized or nonlyophillized) form for reconstitution at the time of delivery with a suitable vehicle, such as sterile water.

Topical applications may be formulated in hydrophobic or hydrophilic bases as ointments, creams, lotions, paints, or powders.

Oral compositions may take such forms as tablets, capsules, oral suspensions and oral solutions. The oral compositions may utilize conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ a dosage amount in the range of from about 250 mg to 1000 mg. In parenteral administration, the unit dosage will typically include the pure compound in sterile water solution or in the form of a soluble powder intended for solution, which can be adjusted to neutral pH and isotonic.

The preferred methods of administration of the Formula I antibacterial compounds include oral,and parenteral, e.g., i.v. infusion, i.v. bolus and i.m. injection.

For adults, about 5–50 mg; of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. The compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary i be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

Preparation of Tetralone Derivative

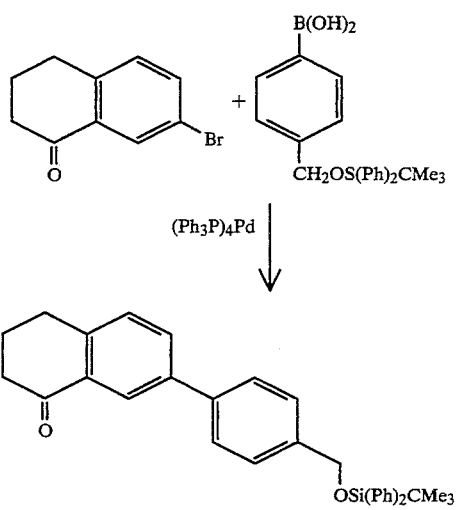

The 7-bromo-1-tetralone (2.07 g, 9.21 mmole), the boronic acid derivative(5.4 g, 13.8 mmole), from example tetrakistriphenyl-phosphinepalladium (531 mg, 0.46 mmole), and 8.4 mL(16.8 mmole) of a 2.0M aqueous solution of sodium carbonate were combined and stirred in 20 mL of toluene and 10 mL of ethanol at reflux for 3 hour. The cooled mixture was partitioned between diethyl ether and water and the organic phase was separated, washed with brine, dried over anhydrous sodium sulfate, filtered, and evaporated. Purification by column chromatography on silica gel eluted with dichloromethane-pet. ether(1:1) gave 4.53 g (100%) of the product.

$^1$H NMR(CDCl$_3$) δ: 1.12(s, 9H), 2.18(p, J=6Hz, 2H), 2.71(t, J=6Hz, H), 3.02(t, J=6Hz, 2H), 7.32–7.76(m, :16H), and 8.3(d, J=2Hz, 1H).

PREPARATIVE EXAMPLE 2

Preparation of Tetralone Stannane

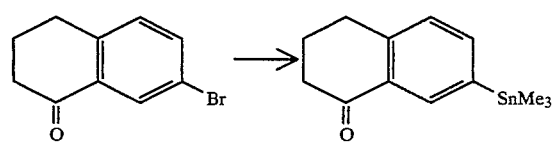

The 7-bromo-1-tetralone (225 mg, 1.0 mmole), 655.2 mg (2.0 mmole) of hexamethylditin, is tetrakistriphenyl-phosphinepalladium (57.7 mg, 0.05 mmole), and 26.2 mg (0.1 mmole) of triphenylphosphine were combined and stirred in 3 mL of toluene at 100° C. for 1 hour. The cooled mixture was partitioned between ethyl acetate and ice-water and the organic phase was separated, washed with brine, dried over anhydrous sodium sulfate, filtered, and evaporated. Purification by plate-layer chromatography on silica gel eluted with dichloromethane-pet. ether (2:1) gave 307.2 mg (99%) of the stannane.

$^1$H NMR(CDCl$_3$) δ: 0.16–0.44(m, 9H), 2.16(p, J=6Hz, 2H), 2.69 (t, J=6Hz, 2H), 2.95(t, J=6Hz, 2H), 7.22(d, J=7.9Hz, 1H), 7.6(dd, J=1.2and 7.9Hz, 1H), and 8.16(bs, 1H).

PREPARATIVE EXAMPLE 3

Preparation of Tetralone Derivative

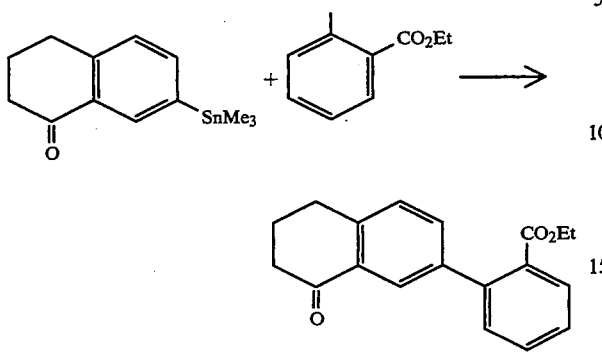

The 7-trimethylstannyl-1-tetralone (294.1 mg, 0.95 mmole), 2.8 mg (0.95 mmole) of ethyl-2-iodo-benzoate,19.8 mg (0.02 mmole) trisdibenzylideneacetonedipalladium-chloroform catalyst and 4.5 mg (0.1 mmole) of diisopropylamrnonium hydrochloride were combined and stirred in 3 mL of N-methylpyrrolidinone at room temperature for 1.5 hour. The mixture was partitioned between diethyl ether and ice-water and the organic phase was separated, washed twice with water and then brine, dried over anhydrous sodium sulfate, filtered, and evaporated. Purification by plate-layer chromatography on silica gel eluted with dichloromethane-pet. ether(3:1) gave 214.7 mg (77%) of the coupled product.

$^1$H NMR(CDCl$_3$) δ: 1.11(t, J=7Hz, 3H), 2.18(p, J=6Hz, 2H), 2.65(t, J=6Hz, 2H), 3.02(t, J=6Hz, 2H), 4.14(q, J=7Hz, 2H),7.29–7.54(m, 5H), 7.87(dd, J=1.9and 6.7Hz, 1H), and 8.0(d, J=1.9Hz, 1H).

IR(CH$_2$Cl$_2$)cm$^{-1}$: 1720 and 1683.

PREPARATIVE EXAMPLE 4

Preparation of Acid Tetralone Derivative

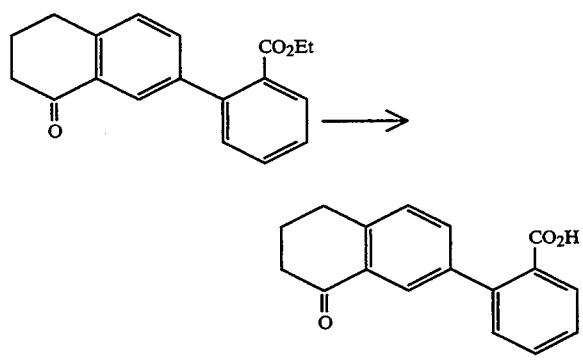

A stirred mixture of 197.6 mg (0.67 mmole) of the tetralone ester derivative and 282.1 μL (1.41 mmole) of 5N NaOH solution in 3 mL of methanol was stirred at ambient temperature for 16 hours, and then refluxed for 3 hours. The cooled mixture was concentrated in vacuo, diluted with water and extracted with ether. The separated aqueous layer was acidified with 2N HCl and extracted with ether. The extract was dried over anhydrous sodium sulfate, filtered, and evaporated to give 112 mg (63%) of the tetralone acid derivative as a colorless foam.

$^1$H NMR (CDCl$_3$) δ: 2.2 (p, J=6Hz, 2H), 2.7 (t, J=6Hz, 2H), 3.02 (t, J=6Hz, 2H), 7.24–7.6 (m, 5H), 7.98 (m, 1H), and 8.04 (m, 1H).

PREPARATIVE EXAMPLE 5

Preparation of 4-t-Butyldiphenylsiloxymethylbromobenzene

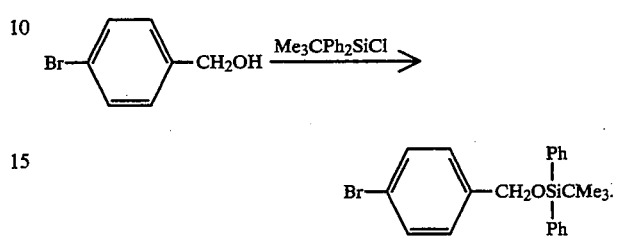

To a stirred solution of 7.48 g (40 mmoles) of p-bromobenzyl alcohol and 6.07 g (60 mmoles) of triethylamine in 70 mL of sieve dried DMF at 0° C. was added 14.3 g (52 mmoles) of neat t-butyldiphenylsilylchloride. The ice-water bath was removed and the mixture was stirred further for 20 hours.

The mixture was partitioned between ether, ice-water, and 2N hydrochloric acid, and the organic phase was separated, washed with water and brine, dried over anhydrous sodium sulfate, filtered, and evaporated.

Purification by column chromatography on 200 g of EM-60 silica gel eluting with hexanes-methylene chloride (3:1) gave 15.9 g (94%) of the title compound.

NMR (CDCl$_3$) δ: 1.1 (s, 9H), 4.72 (s, 2H), 7.22 (d, J=8.3 Hz, 2H), 7.43 (m, 8H), 7.7 (m, 4H).

PREPARATIVE EXAMPLE 6

Preparation of 4-t-butyldiphenylsiloxymethylphenylboronic Acid

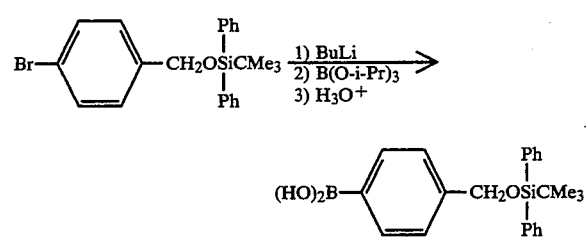

To a stirred solution of p-t-butylidiphenylsiloxymethylbromobenzene (10.1 g, 23.8 mmoles) in 100 mL of dry tetrahydrofuran at −78° C. under nitrogen was added dropwise 9.9 mL (25.0 mmoles) of 2.5M n-butyllithium in hexane. The mixture was stirred at −78° C. for minutes and 4.7 g (25.0 mmoles) of triisopropylborate was added. After 5 minutes, the low temperature bath was removed, and the mixture was stirred further for 1.5 hours.

The mixture was poured onto ice-2N hydrochloric acid and s ether was added. The biphasic mixture was stirred for 0.5 hour and the organic phase was separated, washed with brine, dried over anhydrous sodium sulfate, filtered, and evaporated to give 8.8 g (94.2% of crude product).

Precipitation from an ether-methylene chloride solution of the crude material with hexanes gave 7.1 g (76%) from two crops.

EXAMPLE 1

Preparation of Azetidinone 1

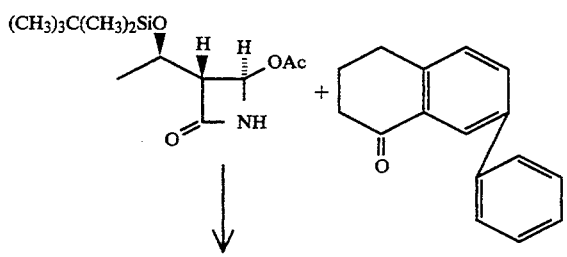

To a stirred mixture of 3.68 g (12.7 mmole) of azetidinone, 4.26 g (19 mmole) of 7-phenyltetralone, and 2.59 g (25.6 mmole) of triethylamine in 50 mL of sieve dried dichloromethane at 0° C. was added 6.26 g (28.1 mmole) of trimethylsilyl triflate. The resulting mixture was stirred under an inert atmosphere of nitrogen at 0° C. for four hours. The mixture was partitioned between diethyl ether, ice-water, and N hydrochloric acid. The organic phase was separated, washed with brine and then saturated sodium bicarbonate and sodium chloride, dried over anhydrous sodium sulfate, filtered, and evaporated.

The residue was purified by silica gel chromatography using toluene-diethyl ether (3:1) as eluant, to give 5.5 g (95%) of the product mixture 1. By a combination of crystallization and silica gel chromatography the individual α and β isomers were separated.

α-Isomer $^1$H NMR(CDCl$_3$) δ: 0.08(s, 3H), 0.1 (s, 3H), 0.9(s, 9H), 1.3(d, 3H), 1.94(m), 2.34(m), 2.58(m), 2.86(m), 3.08(m), 3.76(dd, 1H), 4.22(p, 1H), 6.54(bs, 1H), :7.28–7.8(m, 7H), and 8.22(d, 1H).

IR(CH$_2$Cl$_2$) cm$^{-1}$: 3420, 1755, 1660, and 1620.

MS(m/e): 392[M+—C(CH$_3$)$_3$].

β-Isomer $^1$H NMR(CDCl$_3$) δ: 0.1 (s, 6H), 0.88(s, 9H), 1.28(d, 3H), 1.98–2.42(m, 2H), 2.76(m, 1H), 3.1(m, 3H)! 4.3(p, 1H), 4.48(t, 1H), 5.96(bs, 1H), 7.3–7.8(m, 7H), and 8.22(d, 1H).

IR(CH$_2$Cl$_2$) cm$^{-1}$: 3410, 1760, 1660, and 1620.

MS(m/e): 392[M+—C(CH$_3$)$_3$].

α and β isomers refer to the carbon atom attached to C-4 of the azetidinone ring.

EXAMPLE 1A

Preparation of Azetidinones

In a manner analogous to Example 1, the following azetidinones were prepared:

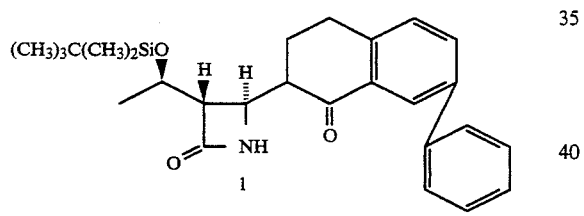

| | YIELDS (%) | $^1$HNMR SHIFT(δ) H-4 | |
|---|---|---|---|
| | | α-ISOMER | β-ISOMER |
| | 80 | 3.76 | 4.47 |
| | 70 | 3.70 | 4.28 |

PG = Si(Me)$_2$CMe$_3$

EXAMPLE 2

Synthesis of Oxalimide 2

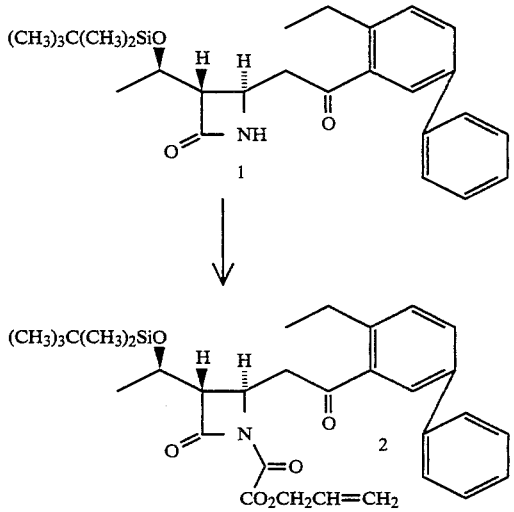

To a stirred solution of 449 mg (1 mmole) of [β-isomeric azetidinone 1, from example 1, and 316.4 mg (4 mmole) of pyridine in 4 mL of sieve dried dichloromethane at 0° C. under an atmosphere of nitrogen was added 1.5 mL of a 2M 2stock solution of allylchlorooxalate in dichloromethane. The resulting mixture was stirred at 0° C. for 0.5 hour and then partitioned between diethyl ether, ice-water, and pH 7 phosphate buffer. The organic phase was separated, washed with brine, dried over anhydrous sodium sulfate, filtered, evaporated, and dried in vacuo to provide 568 mg of crystalline solid 2.

$^1$H NMR(CDCl$_3$) δ: 0.06(s, 6H), 0.85(s, 9H), 1.2(d, J=6.3Hz, 3H), 2.04–2.3(m, 2H), 3.1–3.3(m, 4H), 4.3(m, 1H), 4.68(t, J=3.4Hz, 1H), 4.8(m, 2H), 5.28–5.45(m, 2H), 5.9–5.99(m, 1H), 7.26–7.76(m, 7H), and 8.28(bs, 1H).

IR(CH$_2$Cl$_2$) cm$^{-1}$: 1810, 1752, 1680, and 1620.

EXAMPLE 3

Synthesis of Phosphorane 3

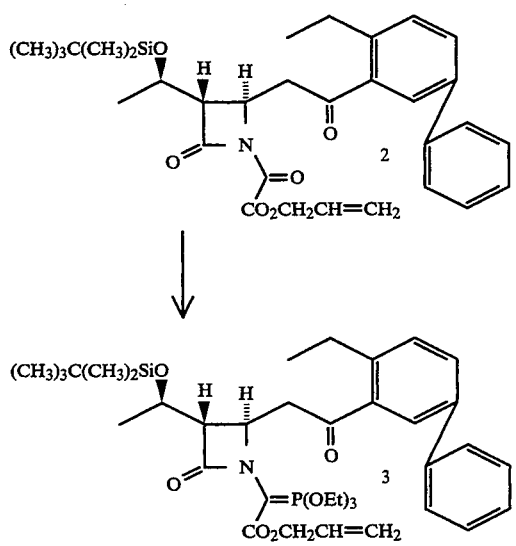

The oxalimide 2 (567.4 mg, 1 mmole), from example 2, and triethylphosphite (1.68 g, 10 mmole) in 5 mL p-xylene was stirred at 120° C. under an inert atmosphere of nitrogen for 1.5 hours. The cooled mixture was rotoevaporated under high vacuum and dried further in vacuo to provide a quantitative amount of phosphorane product 3, which was used immediately without further purification.

EXAMPLE 4

Preparation of Carbapenem 4

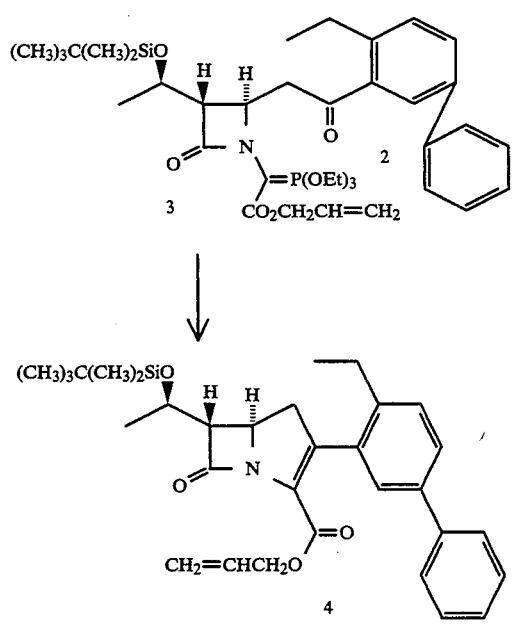

A stirred solution of phosphorane 3 (719.1 mg, 1 mmole), from Example 3, with a crystal of hydroquinone in 25 mL of p-xylene was kept at 140° C. under an atmosphere of nitrogen for hours. The cooled solution was evaporated and the residue purified by plate layer chromatography [one development pet. ether-ether(3:1)] to give 353 mg (66%) of 4 as a yellow foam.

$^1$H NMR(CDCl$_3$) δ: 0.097(s, 6H), 0.9(s, 9H), 1.27(d, J-6.1Hz, 3H), 1.94–2.1(m, 2H), 3.06–3.2(m, 3H), 3.25(dd, J- 3.2 and 6.1Hz, 1H), 4.3(m, 1H), 4.32(dd, J=3.2 and 7.5Hz, 1H), 4.7(m, 2H), 5.1–5.42(m, 2H), 5.8–6.02(m, 1H), 7.16–7.6(m, 7H), and 8.0(d, J=1.5Hz,1H).

IR(CH$_2$Cl$_2$) cm$^{-1}$: 1775 and 1718.
UV(dioxane) nm: 326, 269.
MS(m/e): 529(M+).

EXAMPLE 4A

Preparation of Carbapenems

Using the procedures of examples 2, 3, and 4, the following quadracyclic carbapenems were prepared:

|  | OVERALL YIELD(%) | CYLIZATION TIME(HR) | $^1$HNMR SHIFT(δ) H-5 | H-8 |
|---|---|---|---|---|
| (structure) | 27 | 20 | 4.33 | 8.02 |

-continued

| | OVERALL YIELD(%) | CYLIZATION TIME(HR) | $^1$HNMR SHIFT(δ) | |
|---|---|---|---|---|
| | | | H-5 | H-8 |
| 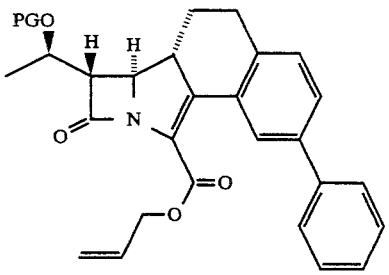 | 28 | 96 | 3.81 | 8.79 |

PG = Si(Me)$_2$CMe$_3$

EXAMPLE 4B

Preparation of Carbapenems

Using the procedures of examples 2, 3, and 4, the following quadracyclic carbapenems are prepared:

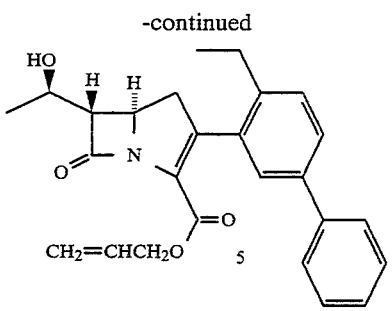

| m | n | X | R$^a$ | Position R$^a$ |
|---|---|---|---|---|
| 1 | 1 | bond | CH$_2$OSiPh$_2$CMe$_2$ | 7' |
| 1 | 1 | bond | CH$_2$OSiPh$_2$CMe$_2$ | 8' |
| 1 | 1 | bond | CH$_2$OSiPh$_2$CMe$_2$ | 6' |
| 1 | zero | O | CH$_2$OSiPh$_2$CMe$_2$ | 7' |
| 1 | zero | S | CH$_2$OSiPh$_2$CMe$_2$ | 7' |
| 1 | zero | SO$_2$ | CH$_2$OSiPh$_2$CMe$_2$ | 7' |
| 1 | zero | C(OCH$_2$)$_2$ | CH$_2$OSiPh$_2$CMe$_2$ | 7' |
| 1 | zero | NCO$_2$allyl | CH$_2$OSiPh$_2$CMe$_2$ | 7' |
| 1 | zero | CH=CH | CH$_2$OSiPh$_2$CMe$_2$ | 7' |
| 1 | 1 | C(O)NH | CH$_2$OSiPh$_2$CMe$_2$ | 7' |
| 2 | 1 | bond | CH$_2$OSiPh$_2$CMe$_2$ | 7' |

EXAMPLE 5

Preparation of Carbapenem 5

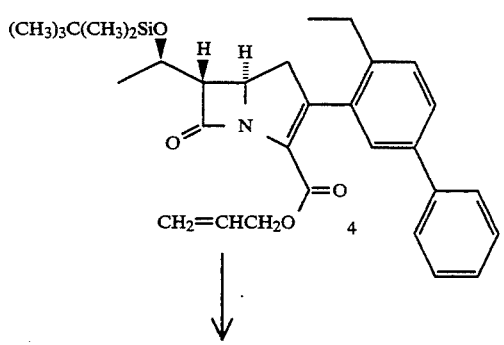

To a stirred solution of 4 (98.7 mg, 0.19 mmole) in 1 mL of tetrahydrofuran at room temperature under an atmosphere of nitrogen was added sequentially neat glacial acetic acid (39.2 mg, 0.65 mmole) and 0.56 mL (0.56 mmole) of a 1M solution of tetrabutylammonium fluoride in THF. The mixture was stirred at ambient temperature for 24 hours.

The mixture was partitioned between ethyl acetate, ice-water, and saturated sodium bicarbonate solution and the organic phase was separated, washed with brine, dried over anhydrous sodium sulfate, filtered, and evaporated.

Purification by plate layer chromatography [one development CH$_2$Cl$_2$-ether(3:1)] gave 45.1 mg (58%) of product 5.

1H NMR(CDCl$_3$) δ: 1.36(d, J=6.2Hz, 3H), 1.94–2.2(m, 3H), 3.08–3.28(m, 3H), 3.33(dd, J=3.2 and 6.6Hz, 1H), 4.28(m, 1H), 4.36(dd, J=3.2 and 7.5Hz, 1H), 4.7(m, 2H), 5.1–5.4(m, 2H), 5.8–6.02(m, 1H), 7.12–7.6(m, 7H),and 8.0(d, J=1.5Hz, 1H).

IR(CH$_2$Cl$_2$) cm$^{-1}$: 3600, 1775 and 1720.
UV(dioxane) nm: 326, 254.
MS(m/e): 415(M+).

EXAMPLE 5A

Preparation of Carbapenems

Following the procedure of example 5, the following quadracyclic carbapenems were prepared:

| | YIELD(%) | ¹HNMR SHIFT(δ) | |
|---|---|---|---|
| | | H-5 | H-8 |
| [structure 1] | 28 | 4.37 | 8.03 |
| [structure 2] | 53 | 3.85 | 8.72 |

EXAMPLE 5B

Preparation of Carbapenems

Using the procedure of Example 5, the following quadracyclic carbapenems are prepared:

| m | n | X | R$^a$ | Position R$^a$ |
|---|---|---|---|---|
| 1 | 1 | bond | CH$_2$OH | 7' |
| 1 | 1 | bond | CH$_2$OH | 8' |
| 1 | 1 | bond | CH$_2$OH | 6' |
| 1 | zero | O | CH$_2$OH | 7' |
| 1 | zero | S | CH$_2$OH | 7' |
| 1 | zero | SO$_2$ | CH$_2$OH | 7' |
| 1 | zero | C(OCH$_2$)$_2$ | CH$_2$OH | 7' |
| 1 | zero | NCO$_2$allyl | CH$_2$OH | 7' |
| 1 | zero | CH=CH | CH$_2$OH | 7' |
| 1 | 1 | —C(O)NH— | CH$_2$OH | 7' |
| 2 | 1 | bond | CH$_2$OH | 7' |

EXAMPLE 6

Preparation of Carbapenem Derivative 6

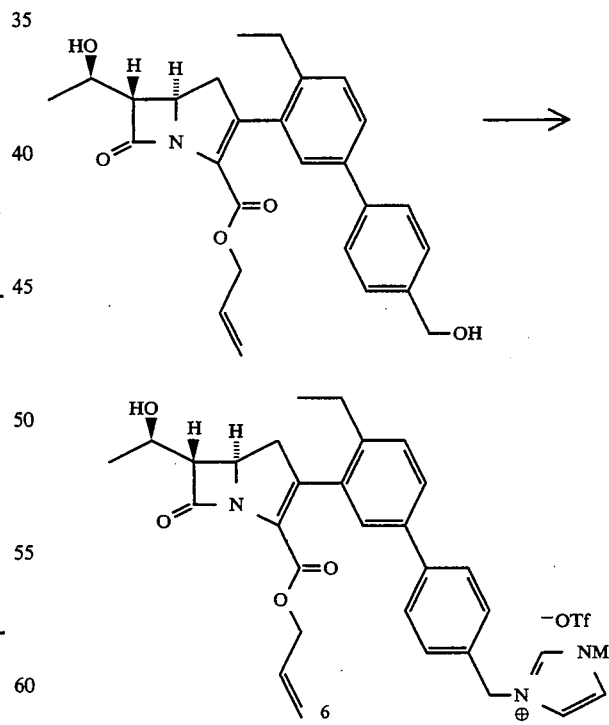

To a stirred solution of 22.6 mg (0.05 mmole) of diol in 0.5 ml of methylene chloride at −23° C. under nitrogen was added sequentially 8.8 mg (0.1 mmole) of N-methylimidazole and then mg (0.053 mmole) of triflic anhydride. The resulting mixture was stirred further for 3 hours.

The mixture was partitioned between methylene chloride and water, and the organic phase separated, dried over anhydrous sodium sulfate, filtered, and evaporated. The residue was dissolved in a minimum amount of methylene chloride and the product was precipitated by the addition of diethyl ether; repetition, and drying in vacuo gave 24.6 mg (86%) of 6.

$^1$H NMR(CDCl$_3$-d$_6$-Acetone) δ: 1.2(d, CH$_3$), 3.8(s, N—CH$_3$), and 9.1(bs).

EXAMPLE 6A,

Preparation of Carbapenems

Using the procedure of example 6, the following quadracyclic carbapenems are prepared:

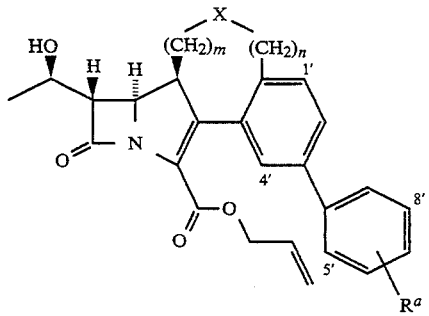

| m | n | X | R$^a$ | Position R$^a$ |
|---|---|------|---------------------------------|----|
| 1 | 1 | bond | CH$_2$—N$^\oplus$(=\)NMe  $^\ominus$OTf | 7' |
| 1 | 1 | bond | CH$_2$—N$^\oplus$(=\)NMe  $^\ominus$OTf | 8' |
| 1 | 1 | bond | CH$_2$—N$^\oplus$(=\)N(CH$_2$)$_2$CN  $^\ominus$OTf | 7' |
| 1 | 1 | bond | CH$_2$—N$^\oplus$(=\)N(CH$_2$)$_2$OSiEt$_3$  $^\ominus$OTf | 7' |
| 1 | 1 | bond | CH$_2$—N$^\oplus$(=\)N(CH$_2$)$_2$CONH$_2$  $^\ominus$OTf | 7' |
| 1 | 1 | bond | CH$_2$—N$^\oplus$=N—NMe  $^\ominus$OTf | 7' |
| 1 | 1 | bond | CH$_2$—N$^\oplus$, H$_2$N-  $^\ominus$OTf | 7' |
| 1 | 1 | bond | CH$_2$—N$^\oplus$ (bicyclic)  $^\ominus$OTf | 7' |
| 1 | 1 | bond | CH$_2$—N$^\oplus$  NCH$_3^\oplus$  $^\ominus$2OTf | 7' |
| 1 | 1 | bond | CH$_2$—N(Me)$^\oplus$  NMe$_2^\oplus$  $^\ominus$2OTf | 7' |

-continued

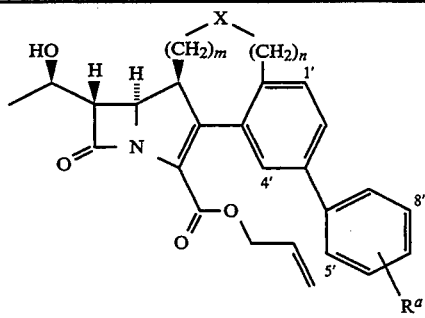

| m | n | X | R$^a$ | Position R$^a$ |
|---|---|---|---|---|
| 1 | 1 | bond | CH$_2$–N$^\oplus$ ... S $^\ominus$OTf | 7' |
| 1 | zero | O | CH$_2$–N$^\oplus$=N–NMe $^\ominus$OTf | 7' |
| 1 | zero | O | CH$_2$–N$^\oplus$=N–NMe $^\ominus$OTf | 7' |
| 1 | zero | O | CH$_2$–N$^\oplus$ ... $^\ominus$OTf, H$_2$N | 7' |
| 1 | zero | O | CH$_2$–N$^\oplus$ ... N$^\oplus$ $^\ominus$OTf | 7' |
| 1 | zero | O | CH$_2$–N$^\oplus$ ... NCH$_3$ $^\oplus$ $^\ominus$2OTf | 7' |
| 1 | zero | O | CH$_2$–N$^\oplus$(Me) ... NMe$_2$ $^\oplus$ $^\ominus$2OTf | 7' |
| 1 | zero | O | CH$_2$–N$^\oplus$ ... S $^\ominus$OTf | 7' |
| 1 | zero | S | CH$_2$–N$^\oplus$=N–NMe $^\ominus$OTf | 7' |
| 1 | zero | S | CH$_2$–N$^\oplus$=N–NMe $^\ominus$OTf | 7' |
| 1 | zero | S | CH$_2$–N$^\oplus$ ... $^\ominus$OTf, H$_2$N | 7' |

-continued

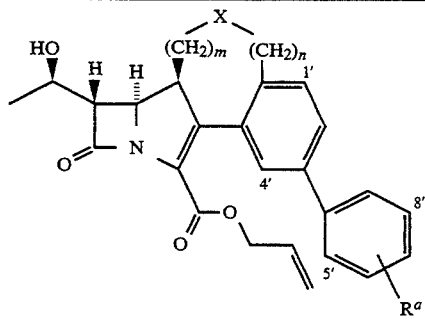

| m | n | X | R$^a$ | Position R$^a$ |
|---|---|---|---|---|
| 1 | zero | S | CH$_2$—N$^\oplus$(bicyclic)⊖OTf | 7' |
| 1 | zero | S | CH$_2$—N$^\oplus$(ring)NCH$_3^\oplus$ ⊖2OTf | 7' |
| 1 | zero | S | CH$_2$—N$^\oplus$(Me)(ring)NMe$_2^\oplus$ ⊖2OTf | 7' |
| 1 | zero | S | CH$_2$—N$^\oplus$(ring)S ⊖OTf | 7' |
| 1 | zero | SO$_2$ | CH$_2$—N$^\oplus$=N(ring)NMe ⊖OTf | 7' |
| 1 | zero | SO$_2$ | CH$_2$—N$^\oplus$=N(ring)NMe ⊖OTf | 7' |
| 1 | zero | SO$_2$ | CH$_2$—N$^\oplus$(ring, H$_2$N)⊖OTf | 7' |
| 1 | zero | SO$_2$ | CH$_2$—N$^\oplus$(bicyclic)⊖OTf | 7' |
| 1 | zero | SO$_2$ | CH$_2$—N$^\oplus$(ring)NCH$_3^\oplus$ ⊖2OTf | 7' |
| 1 | zero | SO$_2$ | CH$_2$—N$^\oplus$(Me)(ring)NMe$_2^\oplus$ ⊖2OTf | 7' |
| 1 | zero | SO$_2$ | CH$_2$—N$^\oplus$(ring)S ⊖OTf | 7' |

-continued

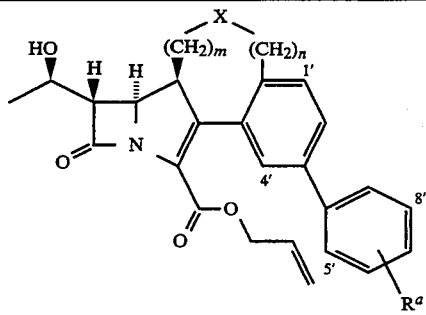

| m | n | X | R$^a$ | Position R$^a$ |
|---|---|---|---|---|
| 1 | zero | NCO$_2$allyl | CH$_2$—N$^\oplus$=N—NMe $^\ominus$OTf (pyrazolium) | 7' |
| 1 | zero | NCO$_2$allyl | CH$_2$—N$^\oplus$=N—NMe $^\ominus$OTf (pyrazolium) | 7' |
| 1 | zero | NCO$_2$allyl | CH$_2$—N$^\oplus$, H$_2$N, $^\ominus$OTf (aminopyridinium) | 7' |
| 1 | zero | NCO$_2$allyl | CH$_2$—N$^\oplus$ bicyclic $^\ominus$OTf | 7' |
| 1 | zero | NCO$_2$allyl | CH$_2$—N$^\oplus$—NCH$_3$$^\oplus$ $^\ominus$2OTf | 7' |
| 1 | zero | NCO$_2$allyl | CH$_2$—N$^\oplus$(Me)—NMe$_2$$^\oplus$ $^\ominus$2OTf | 7' |
| 1 | zero | NCO$_2$allyl | CH$_2$—N$^\oplus$—S $^\ominus$OTf (thiazolium) | 7' |
| 1 | zero | CH=CH | CH$_2$—N$^\oplus$=N—NMe $^\ominus$OTf | 7' |
| 1 | zero | CH=CH | CH$_2$—N$^\oplus$=N—NMe $^\ominus$OTf | 7' |
| 1 | zero | CH=CH | CH$_2$—N$^\oplus$, H$_2$N, $^\ominus$OTf | 7' |
| 1 | zero | CH=CH | N$^\oplus$ bicyclic $^\ominus$OTf | 7' |

-continued

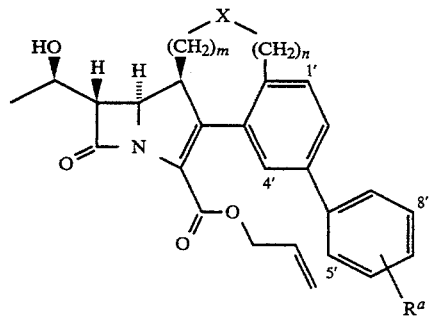

| m | n | X | R<sup>a</sup> | Position R<sup>a</sup> |
|---|---|---|---|---|
| 1 | zero | CH=CH | CH₂−N⊕(ring)NCH₃⊕ ⊖2OTf | 7' |
| 1 | zero | CH=CH | CH₂−N⊕(Me)(ring)NMe₂⊕ ⊖2OTf | 7' |
| 1 | zero | CH=CH | CH₂−N⊕(ring)S ⊖OTf | 7' |
| 1 | zero | O=CNH− | CH₂−N⊕=N(ring)NMe ⊖OTf | 7' |
| 1 | zero | O=CNH− | CH₂−N⊕=N(ring)NMe ⊖OTf | 7' |
| 1 | zero | O=CNH− | CH₂−N⊕(ring,H₂N) ⊖OTf | 7' |
| 1 | zero | O=CNH− | CH₂−N⊕(bicyclic) ⊖OTf | 7' |
| 1 | zero | O=CNH− | CH₂−N⊕(ring)NCH₃⊕ ⊖2OTf | 7' |
| 1 | zero | O=CNH− | CH₂−N⊕(Me)(ring)NMe₂⊕ ⊖2OTf | 7' |
| 1 | zero | O=CNH− | CH₂−N⊕(ring)S ⊖OTf | 7' |
| 2 | 1 | bond | CH₂−N⊕=N(ring)NMe ⊖OTf | 7' |

-continued

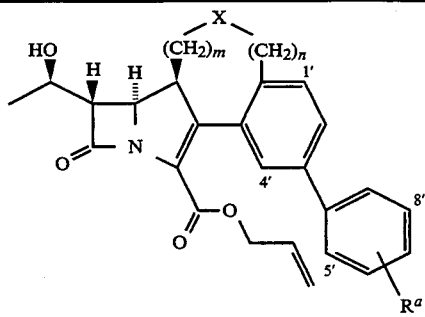

| m | n | X | $R^a$ | Position $R^a$ |
|---|---|---|---|---|
| 2 | 1 | bond | CH$_2$—N$^⊕$=N—NMe  ⊖OTf (pyrazolium) | 7' |
| 2 | 1 | bond | CH$_2$—N$^⊕$ (pyridinium, H$_2$N substituted)  ⊖OTf | 7' |
| 2 | 1 | bond | CH$_2$—N$^⊕$ (bicyclic azabicyclo)  ⊖OTf | 7' |
| 2 | 1 | bond | CH$_2$—N$^⊕$(piperazinium)NCH$_3^⊕$  ⊖2OTf | 7' |
| 2 | 1 | bond | CH$_2$—N$^⊕$(Me)(piperidinium)NMe$_2^⊕$  ⊖2OTf | 7' |
| 2 | 1 | bond | CH$_2$—N$^⊕$=N—NMe  ⊖OTf (triazolium) | 7' |

EXAMPLE 7

Preparation of Carbapenem Derivative 7

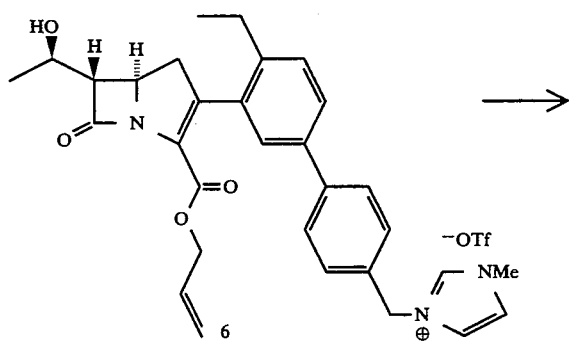 → 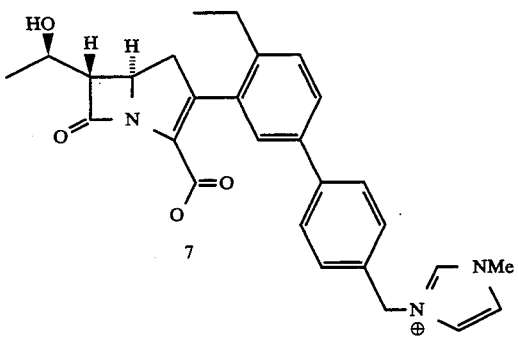

To a stirred solution of 24.6 mg (0.044 mmole) of salt 6 in 1.0 ml of methylene chloride at room temperature was added 6.9 mg (0.026 mmole) of triphenylphosphine, 10.1 mg (0.0088 mmole) of tetrakistriphenylphosphinepalladium(O), and 96.5 μL(0.048 mmole) of a 0.5M solution of sodium-2-ethylhexanoate. The resulting mixture was stirred under nitrogen for 0.5 hours.

The mixture was chilled in an ice-water bath and diethyl ether was added. The separated material was collected by centrifugation and decantation of the supernatant. The crude product was washed analogously with ether and dried in vacuo to give 26.8 mg of residue. Purification by reverse phase plate layer chromatography one development H$_2$)—CH$_3$CN(7:3)] gave after extraction, concentration, and lyophilization 3.3 mg (16%) of product 7.

$^1$H NMR[D$_2$O—CD3CN(5:2)] δ: 1.5(d, 3H), 2.1–2.4(m, 2H), 3.28–3.6(m, 3H), 3.8(m, 1H), 4.1(s, N—CH$_3$), 4.5–4.7(m, 2H), 4.8(s,HDO), 5.67(s, 2H), 7.5–8.1(m, 9H), and 9.0(bs).

UV(H$_2$O): λ$_{max}$ 303,265 nm.

EXAMPLE 7A

Preparation of Carbapenems

Using the procedure of example 7, the following quadracyclic carbapenems are prepared:

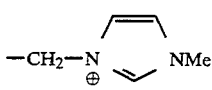

| m | n | X | R$^a$ | Position R$^a$ |
|---|---|------|------|------|
| 1 | 1 | bond | —CH$_2$—N$^⊕$(imidazole)NMe | 7' |
| 1 | 1 | bond | —CH$_2$—N$^⊕$(imidazole)NMe | 8' |
| 1 | 1 | bond | —CH$_2$—N$^⊕$(imidazole)N(CH$_2$)$_2$CN | 7' |
| 1 | 1 | bond | —CH$_2$—N$^⊕$(imidazole)N(CH$_2$)$_2$OH | 7' |
| 1 | 1 | bond | —CH$_2$—N$^⊕$(imidazole)N(CH$_2$)$_2$CONH$_2$ | 7' |
| 1 | 1 | bond | CH$_2$—N$^⊕$=N(triazole)NMe | 7' |
| 1 | 1 | bond | CH$_2$—N$^⊕$(pyridine)-NH$_2$ | 7' |
| 1 | 1 | bond | CH$_2$—N$^⊕$(DABCO) | 7' |
| 1 | 1 | bond | CH$_2$—N$^⊕$(piperazine)NCH$_3^⊕$ ⊖Cl | 7' |

-continued

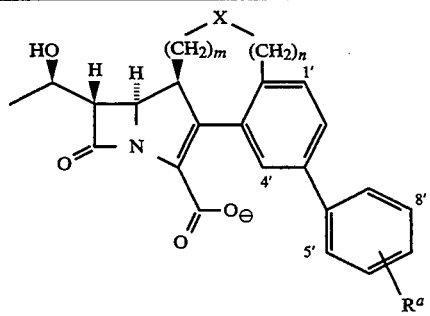

| m | n | X | R$^a$ | Position R$^a$ |
|---|---|---|---|---|
| 1 | 1 | bond | CH$_2$—N$^⊕$(Me)—CH$_2$CH$_2$—N$^⊕$Me$_2$ ⊖Cl | 7' |
| 1 | 1 | bond | CH$_2$—N$^⊕$(thiazole ring with S) | 7' |
| 1 | zero | O | CH$_2$—N$^⊕$—NMe (imidazole) | 7' |
| 1 | zero | O | CH$_2$—N$^⊕$=N—NMe (triazole) | 7' |
| 1 | zero | O | CH$_2$—N$^⊕$(pyridine)—H$_2$N | 7' |
| 1 | zero | O | CH$_2$—N$^⊕$(quinuclidine) | 7' |
| 1 | zero | O | CH$_2$—N$^⊕$—CH$_2$CH$_2$—N$^⊕$HCH$_3$ ⊖Cl | 7' |
| 1 | zero | O | CH$_2$—N$^⊕$(Me)—CH$_2$CH$_2$—N$^⊕$Me$_2$ ⊖Cl | 7' |
| 1 | zero | O | CH$_2$—N$^⊕$(thiazole, S) | 7' |
| 1 | zero | S | CH$_2$—N$^⊕$—NMe (imidazole) | 7' |
| 1 | zero | S | CH$_2$—N$^⊕$=N—NMe (triazole) | 7' |

-continued
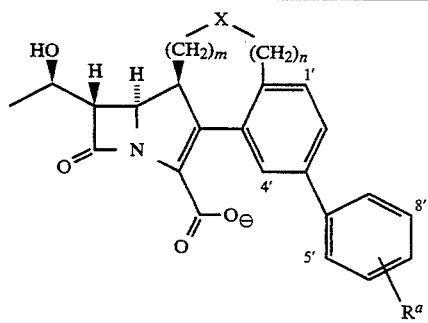
| m | n | X | Rª | Position Rª |
|---|---|---|---|---|
| 1 | zero | S | CH₂—N⁺(pyridinium)-NH₂ | 7' |
| 1 | zero | S | CH₂—N⁺(azabicyclic) | 7' |
| 1 | zero | S | CH₂—N⁺(CH₂CH₂)₂N⁺HCH₃ ⊖Cl | 7' |
| 1 | zero | S | CH₂—N⁺(Me)(CH₂CH₂)₂N⁺Me₂ ⊖Cl | 7' |
| 1 | zero | S | CH₂—N⁺(thiazolium) S | 7' |
| 1 | zero | SO₂ | CH₂—N⁺ NMe | 7' |
| 1 | zero | SO₂ | CH₂—N⁺=N NMe | 7' |
| 1 | zero | SO₂ | CH₂—N⁺(pyridinium)-NH₂ | 7' |
| 1 | zero | SO₂ | CH₂—N⁺(azabicyclic) | 7' |
| 1 | zero | SO₂ | CH₂—N⁺(CH₂CH₂)₂N⁺HCH₃ ⊖Cl | 7' |

-continued

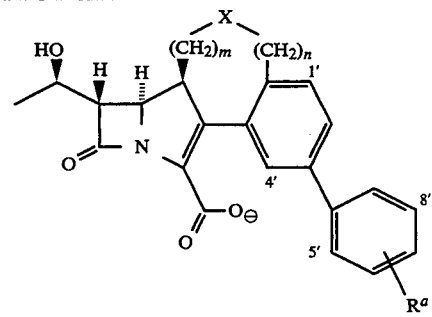

| m | n | X | R$^a$ | Position R$^a$ |
|---|---|---|---|---|
| 1 | zero | SO$_2$ | CH$_2$–N$^⊕$(Me)–CH$_2$CH$_2$CH$_2$–N$^⊕$Me$_2$  $^⊖$Cl | 7' |
| 1 | zero | SO$_2$ | CH$_2$–N$^⊕$ (ring with S) | 7' |
| 1 | zero | NH | CH$_2$–N$^⊕$ (ring with NMe) | 7' |
| 1 | zero | NH | CH$_2$–N$^⊕$=N (ring with NMe) | 7' |
| 1 | zero | NH | CH$_2$–N$^⊕$ (ring with H$_2$N) | 7' |
| 1 | zero | NH | CH$_2$–N$^⊕$ (saturated ring) | 7' |
| 1 | zero | NH | CH$_2$–N$^⊕$–CH$_2$CH$_2$CH$_2$–NCH$_3$$^⊕$  $^⊖$Cl | 7' |
| 1 | zero | NH | CH$_2$–N$^⊕$(Me)–CH$_2$CH$_2$CH$_2$–NMe$_2$$^⊕$Me  $^⊖$Cl | 7' |
| 1 | zero | NH | CH$_2$–N$^⊕$ (ring with S) | 7' |
| 1 | zero | CH=CH | CH$_2$–N$^⊕$ (ring with NMe) | 7' |
| 1 | zero | CH=CH | CH$_2$–N$^⊕$=N (ring with NMe) | 7' |

-continued

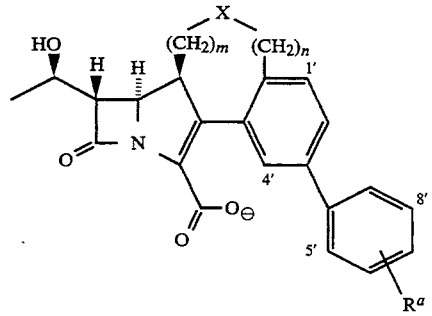

| m | n | X | $R^a$ | Position $R^a$ |
|---|---|---|---|---|
| 1 | zero | CH=CH | CH₂—N⁺(pyridinyl)–NH₂ | 7' |
| 1 | zero | CH=CH | CH₂—N⁺(bicyclic) | 7' |
| 1 | zero | CH=CH | CH₂—N⁺(CH₂CH₂)₂NCH₃⁺ ⊖Cl | 7' |
| 1 | zero | CH=CH | CH₂—N⁺(Me)(CH₂CH₂)₂NMe₂⁺ ⊖Cl | 7' |
| 1 | zero | CH=CH | CH₂—N⁺(thiazolyl)S | 7' |
| 1 | zero | O=CNH— | CH₂—N⁺(pyrazinyl)NMe | 7' |
| 1 | zero | O=CNH— | CH₂—N⁺=N(triazinyl)NMe | 7' |
| 1 | zero | O=CNH— | CH₂—N⁺(pyridinyl)–NH₂ | 7' |
| 1 | zero | O=CNH— | CH₂—N⁺(bicyclic) | 7' |
| 1 | zero | O=CNH— | CH₂—N⁺(CH₂CH₂)₂NCH₃⁺ ⊖Cl | 7' |

-continued

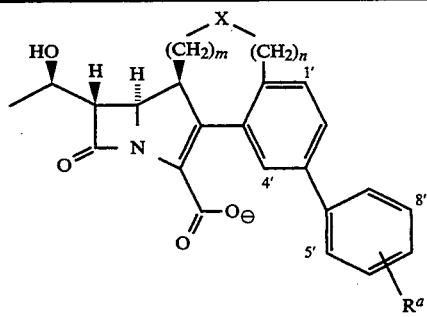

| m | n | X | R$^a$ | Position R$^a$ |
|---|---|---|---|---|
| 1 | zero | O=CNH— | CH$_2$–N$^⊕$(Me)–CH$_2$CH$_2$CH$_2$–N$^⊕$Me$_2$  ⊖Cl | 7' |
| 1 | zero | O=CNH— | CH$_2$–N$^⊕$ (thiazine ring with S) | 7' |
| 2 | 1 | bond | CH$_2$–N$^⊕$ (ring)–NMe | 7' |
| 2 | 1 | bond | CH$_2$–N$^⊕$=N (ring)–NMe | 7' |
| 2 | 1 | bond | CH$_2$–N$^⊕$ (ring with H$_2$N substituent) | 7' |
| 2 | 1 | bond | CH$_2$–N$^⊕$ (bicyclic) | 7' |
| 2 | 1 | bond | CH$_2$–N$^⊕$–CH$_2$CH$_2$CH$_2$–N$^⊕$H CH$_3$  ⊖Cl | 7' |
| 2 | 1 | bond | CH$_2$–N$^⊕$(Me)–CH$_2$CH$_2$CH$_2$–N$^⊕$Me$_2$  ⊖Cl | 7' |
| 2 | 1 | bond | CH$_2$–N$^⊕$ (thiazine ring with S) | 7' |

What is claimed is:
1. A compound represented by formula I:

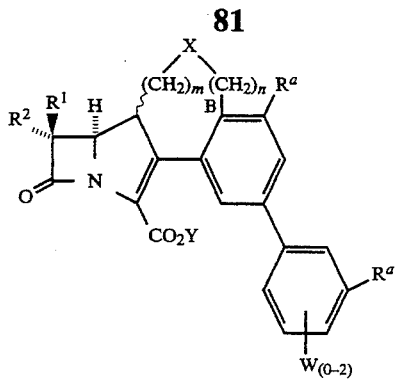

wherein:
m is an integer 0, 1, 2, 3, 4 or 5;
n is an integer 0, 1, 2, 3 or 4;
X represents (a) a bond; (b) —O—; (c) —S(O)$_x$— with x equal to 0, 1 or 2; (d) —C(O)—; (e) —NR'—; (f) —CH=CH—; (g) —C(O)NR'—; (h) —NR'C(O)—; (i) —CO$_2$—; (j) —OC(O)—; (k) —SO$_2$NR'— or (l) —NR'SO$_2$— with R' representing H, C$_1$ to C$_4$ alkyl or acetyl;
the values of m, n and X being selected such that ring B constitutes a 6 to 10 membered ring;
Y represents H, a pharmaceutically acceptable ester, a biolabile ester, a carboxylate protecting group or a metal cation;
R$^1$ and R$^2$ independently represent H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$— or (CH$_3$)$_2$CF—;
one of the R$^a$ groups represents H or W as defined below, and the other represents one of the groups (a) through (d):

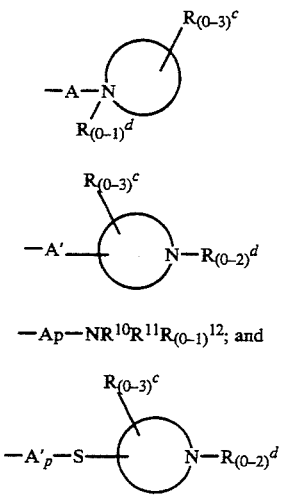

(a)

(b)

—A$_p$—NR$^{10}$R$^{11}$R$_{(0-1)}$$^{12}$; and (c)

(d)

when one of the R$^a$ groups represents

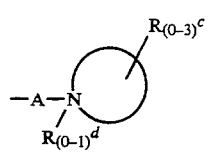

(a)

A represents —(CR$^3$R$^4$)$_r$—Q— (CR$^3$R$^4$)$_s$— wherein r is 0–6, s is 1–6 and Q represents a member selected from the group consisting of: a covalent bond, —O—, —S(O)$_x$— with x equal to 0, 1 or 2, —NR$^3$—, —SO$_2$NR$^3$—, —NR$^3$SO$_2$—, —C(O)NR$^3$—, —NR$^3$C(O)—, —CR$^3$=CR$^4$—, —C(O)— and —OC(O)—;
with R$^3$ and R$^4$ independently representing H or C$_{1-4}$ lower alkyl, and (CR$^3$R$^4$)$_s$— being attached to the ring nitrogen;

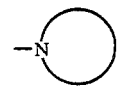

represents a 5 or 6 membered monocyclic heterocycle or an 8–10 membered bicyclic heterocycle, bonded to A through the ring nitrogen and having a substituent group R$^d$ optionally attached to the ring nitrogen, and having 0–3 R$^c$ groups attached to other atoms of the heterocyclic group, said ring nitrogen being tertiary or quaternary by virtue of A, the ring bonds and R$^d$ which may be optionally attached, said heterocyclic group being aromatic, partially aromatic or non-aromatic,
said heterocycle also containing 0–3 additional nitrogen atoms and 0–1 oxygen or sulfur atom;
each R$^c$ independently represents W as defined below or NR$^y$R$^z$, wherein R$^y$ and R$^z$ independently represent H, C$_1$ to C$_4$ alkyl, C$_1$ to C$_4$ alkyl substituted with R$^q$, or R$^y$ and R$^z$ are taken together to represent either a 3- to 5-membered alkylidene radical to form a ring, optionally substituted with R$^q$, or a 2- to 4-membered alkylidene radical interrupted by O or S(O)$_x$ with x equal to 0, 1 or 2, to form a ring, said alkylidene being optionally substituted with R$^q$;
R$^q$ is selected from the group consisting of: hydroxy, methoxy, cyano, —C(O)NH$_2$, —OC(O)NH$_2$, —CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —SO$_3$M$^b$ with M$^b$ representing H or alkali metal, —CO$_2$M$^a$, where M$^a$ is H, alkali metal, methyl or phenyl; and tetrazolyl (where the point of attachment is the carbon atom of the tetrazole ring and one of the nitrogen atoms is mono-substituted by M$^a$ as defined above);
each R$^d$ independently represents a member selected from the group consisting of: hydrogen, NH$_2$, O— or C$_1$ to C$_4$ alkyl, optionally mono-substituted with R$^q$ as defined above;
when one R$^a$ group represents

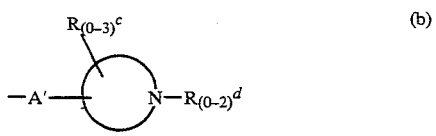

(b)

A' represents —(CR$^3$R$^4$)$_{m'}$—Q—(CR$^3$R$^4$)$_{m'}$— with each m' independently equal to 0–6, and Q, R$^3$ and R$^4$ as defined above, except that when each m' is 0, Q is not a covalent bond, and —(CR$^3$R$^4$)$_{m'}$ attached to the phenyl ring;

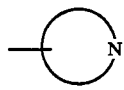

represents a 5 or 6 membered monocyclic heterocycle or an 8–10 membered bicyclic heterocycle, said heterocycle being aromatic, partially aromatic or non-aromatic, bonded to A' through an atom other than the ring nitrogen, and optionally having 0–2 $R^d$ substituent groups attached to the ring nitrogen, said nitrogen in the heterocycle being tertiary or quaternary by virtue of the ring bonds and the optional $R^d$ groups which may be attached;
  said heterocycle further containing 0–1 oxygen or sulfur atom and 0–2 additional nitrogen atoms therein;

$R^c$ and $R^d$ are as defined above;
when one $R^a$ group represents (c) —A-$_p$—NR$^{10}$R$^{11}$R$^{12}$ (0–1);
A is as defined above and p is an integer 0 or 1;
$R^{10}$, $R^{11}$ and where present, $R^{12}$, are independently H, $C_{1-4}$ alkyl or $C_{1-4}$ alkyl mono-substituted with $R^q$;
or $R^{10}$, $R^{11}$ and $R^{12}$ may be taken in combination to represent a $C_4$ to $C_{10}$ alkanetriyl group, optionally substituted with up to three W groups, with W as defined below;
when one $R^a$ group represents (d), A', p, the N containing ring, $R^c$ and $R^d$ are as previously defined;

each W independently represents a member selected from the group consisting of:
a) —$CF_3$;
b) a halogen atom selected from the group consisting of: —Br, —Cl, —F, —I;
c) —$OC_{1-4}$ alkyl, wherein the alkyl is optionally mono-substituted by $R^q$, where $R^q$ is as defined above;
d) —OH;
e) —OC(O)$R^s$, where $R^s$ is $C_{1-4}$ alkyl or phenyl, each of which is optionally mono-substituted by $R^q$ as defined above;
f) —OC(O)N($R^y$)$R^z$, where $R^y$ and $R^z$ are independently H, $C_{1-4}$ alkyl, (optionally mono-substituted by $R^q$ as defined above), or are taken together to represent a 3- to 5-membered alkylidene radical which forms a ring (optionally substituted with $R^q$ as defined above), or a 2- to 4-membered alkylidene radical interrupted by —O—, —S—, —S(O)— or —S(O)$_2$— which forms a ring, said ring being optionally mono-substituted with $R^q$ as defined above;
g) —S(O)$_n$—$R^s$, where n=0–2, and $R^s$ is defined above;
h) —SO$_2$N($R^y$)$R^z$, where $R^y$ and $R^z$ are as defined above;
i) $N_3$
j) —N($R^t$)C(O)H, where $R^t$ is H or $C_{1-4}$ alkyl, said alkyl group being optionally mono-substituted with $R^q$ as defined above;
k) —N($R^t$)C(O)$C_{1-4}$ alkyl, wherein $R^t$ is as defined above;
l) —N($R^t$)C(O)O$C_{1-4}$ alkyl, where $R^t$ is as defined above;
m) —N($R^t$)C(O)N($R^y$)$R^z$ where $R^t$, $R^y$ and $R^z$ are defined above;
n) —N($R^t$)SO$_2$$R^s$, where $R^s$ and $R^t$ are as defined above;
o) —CN;
p) a formyl or acetalized formyl radical which is :—C(O)H or —CH(OCH$_3$)$_2$;
q) —C(OCH$_3$)$_2$ $C_{1-4}$ alkyl, where the alkyl is optionally mono-substituted by $R^q$ as defined above;
r) —C(O)$R^s$, where $R^s$ is as defined above;
s) —(C=NO$R^z$)$R^y$ where $R^y$ and $R^z$ are as defined above, except they may not be joined together to form a ring;
t) —C(O)O$C_{1-4}$ alkyl, where the alkyl is optionally mono-substituted by $R^q$ as defined above;
u) —C(O)N($R^y$)$R^z$, where $R^y$ and $R^z$ are as defined above;
v) —C(O)N(O$R^y$)$R^z$, where $R^y$ and $R^z$ are as defined above, except they may not be joined together to form a ring;
w) —C(S)N($R^y$)$R^z$ where $R^y$ and $R^z$ are as defined above;
x) —COO$M^a$ where $M^a$ is as defined above;
y) —SCN;
z) —SCF$_3$;
aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;
ab) an anionic function selected from the group consisting of:
  P(O)(O$M^a$)$_2$; P(O)(O$M_a$)(O$C_{1-4}$alkyl); P(O)(O$M^a$)($C_{1-4}$ alkyl); P(O)(O$M^a$)NR$^y$R$^z$; P(O)(O$M^a$)NHR$^x$; SO$_2$$M^a$; SO$_3$$M^a$; SO$_2$N$M^a$C(O)NR$^y$R$^z$ and SO$_2$N$M^a$CN wherein
    $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, said $R^q$, $M^a$, $R^y$ and $R^z$ being as defined above;
ac) a $C_5$–$C_7$ cycloalkyl group in which :one of the carbon atoms in the ring is replaced by a heteroatom selected from O, S, NH, or N($C_1$–$C_4$ alkyl) and in which one additional carbon may be replaced by the NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;
ad) a $C_2$–$C_4$ alkenyl radical, optionally mono-substituted by one of the substituents a) to ac) above and phenyl which is optionally substituted by $R^q$ as defined above;
ae) a $C_2$–$C_4$ alkynyl radical, optionally mono-substituted by one of the substituents a) to ac) above;
af) a $C_1$–$C_4$ alkyl radical;
ag) a $C_1$–$C_4$ alkyl group mono-substituted by one of the substituents a)–ac) above;

ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above with the proviso that when R$^a$ contains a quaternary ammonium group Y represents a negative charge.

2. A compound of claim 1, wherein R$^1$ is hydrogen and R$^2$ is (R)CH$_3$CH(OH)— or (R)CH$_3$CH(F)—.

3. A compound of claim 1 wherein R$^a$ is selected from the group consisting of:

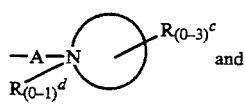
(a)

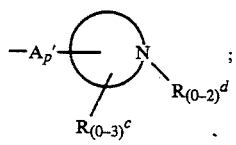
(b)

A and A' represent —CH$_2$—, —CH$_2$CH$_2$— or —CH$_2$CH$_2$CH$_2$—;

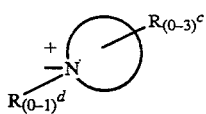

represents a member selected from the group consisting of:

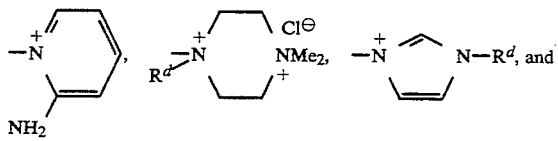

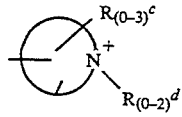

represents a member selected from the group consisting of:

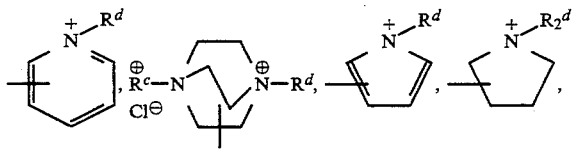

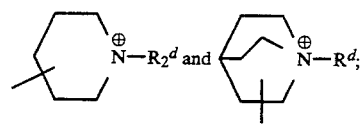

and the point of attachment to —A'— is other than a nitrogen heteroatom.

4. A compound of Claim 1 wherein the group —(CH$_2$)$_m$—X—(CH$_2$)$_n$— represents a member selected from the group consisting of: —CH$_2$—O—; —CH$_2$—S—; —CH$_2$CH$_2$—; —CH$_2$NH—; —CH$_2$SO$_2$—; —CH$_2$C(O)— [or] and —CH$_2$OC(O)—.

5. A compound of claim 2 wherein one R$^a$ represents group (a) or (b), and the other R$^a$ represents a member selected from the group consisting of:

H; —CF$_3$; —Br; —I; —Cl; —F; —OC$_{1-4}$ alkyl; —OC$_{1-4}$ alkyl substituted with 1-3 R$^q$ groups, which are independently selected from —OH, —OCH$_3$, —CN, —F, —CF$_3$, and —COOM$^a$, where M$^a$ is H, alkali metal or methyl; —OH; —S-(O)$_x$R$^s$ with x=0 or 2 and R$^s$ =C$_{1-4}$ alkyl; —C$_{2-4}$ alkenyl; —C$_{2-4}$ alkynyl; —C$_{1-4}$ alkyl substituted with —CF$_3$, —Br, —I, —F, Cl or —OCH$_3$; and —C(O)—C$_{1-4}$ alkyl.

6. A compound of claim 2 wherein one R$^a$ substituent is selected from the group consisting of:

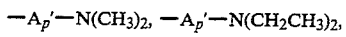

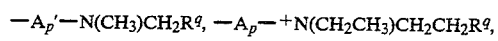

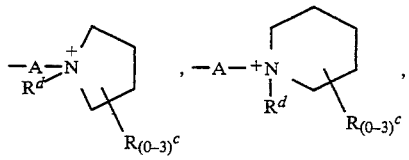

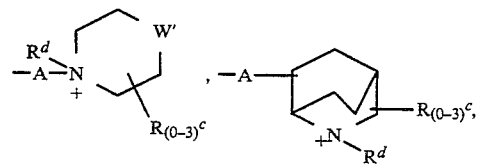

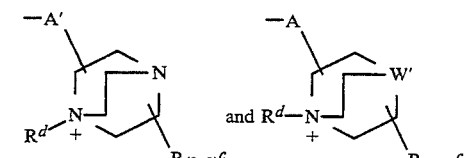

in which W' is O, S, NR', SO or SO$_2$, and where A'$_p$—R$^c$ and are shown to have an indefinite position, they may be attached to any carbon atom of the ring.

7. A compound of claim 1 wherein one R$^a$ group represents one member selected from the group consisting of:

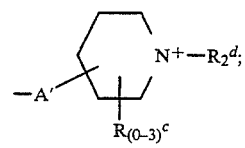

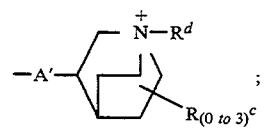

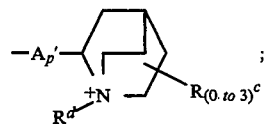

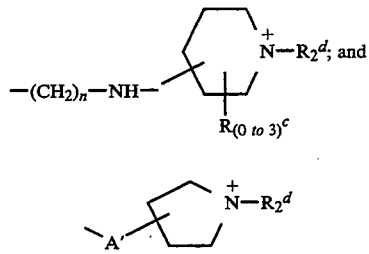

and where $R^d$ and/or A' is shown to have an indefinite position, they may be attached to any carbon atom of the ring.

8. A compound of claim 1 wherein the $R^c$ substituents attached to ring carbon atoms are selected from the group consisting of —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, —CH$_2$CH$_3$, —CH$_2$CONH$_2$ and —CH$_2$CON(C$_1$-C$_4$ alkyl)$_2$
and the $R^c$ substituents attached to ring nitrogen atoms are —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, CH$_2$CH$_2$SO$_3$M$^b$, —CH$_3$, —CH$_2$CH$_3$, —CH$_2$CONH$_2$ and —CH$_2$CON(C$_1$-C$_4$ alkyl).

9. A compound of claim 8 wherein the $R^d$ substituents attached to the nitrogen atom are selected from the group consisting of:
hydrogen, —CH$_3$, —CH$_2$CH$_3$, —CH$_2$CH$_2$CH$_3$, —CH$_2$COOM$^b$, CH$_2$C(O)NH$_2$, —CH$_2$SO$_2$NH$_2$, —CH$_2$SO$_3$M$^b$, —NH$_2$ and —O—.

10. A compound of claim 1 wherein A is selected from the group consisting of:
—CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —SO$_2$NHCH$_2$CH$_2$—, —COCH$_2$—, —CH=CHCH$_2$— and —CH$_2$—O—CH$_2$CH$_2$—.

11. A compound of claim 1 wherein A' is selected from the group consisting of:
—O—, —S—, —NH—, —SO$_2$—, —SO$_2$NH—, —CONH—, —CH=CH—, —CH$_2$S—, —CH$_2$NH—, CONHCH$_2$—, —SO$_2$NHCH$_2$—, —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —SO$_2$NHCH$_2$CH$_2$—, —COCH$_2$—, —CH=CHCH$_2$— and —CH$_2$—O—CH$_2$CH$_2$—.

12. A compound of claim 2 wherein one of the $R^a$ groups represents one of (a) through (d) and the other $R^a$ is independently selected from the group consisting of:

| | |
|---|---|
| —OCH$_3$ | |
| —OCH$_2$CH$_2$OH | —OCH$_2$CO$_2$Me |
| —F | —CF$_3$ |
| —Br | —Cl |
| —OH | —I |
| —OCONH$_2$ | —OCOCH$_3$ |
| —SOCH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |
| —CN | —NHSO$_2$CH$_3$ |
| —COCH$_3$ | —CHO |
| —CH=NOH | —COCH$_2$OH |
| —CH=NOCH$_2$CO$_2$Me | —CH=NOCH$_3$ |
| —SO$_2$CH$_2$CH$_2$OH | —CH=NOCMe$_2$CO$_2$Me |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$Me |
| —CONHOH | —CONHCH$_3$ |
| —tetrazolyl | —CO$_2$Me |
| —SCF$_3$ | —PO$_3$HMe |
| —CONHSO$_2$Ph | —CONHSO$_2$NH$_2$ |
| —SO$_3$Me | —SO$_2$NHCN |
| —SO$_2$NHCONH$_2$ | —CH=CHCN |
| —CH=CHCONH$_2$ | —CH=CHCO$_2$Me |
| —C≡C—CONH$_2$ | —C≡C—CN |
| —CH$_2$OH | —CH$_2$N$_3$ |
| —CH$_2$CO$_2$Me and | —CH$_2$I. |

13. A pharmaceutical composition comprising a compound of claim 1 in combination with a pharmaceutically acceptable carrier.

14. A pharmaceutical composition in accordance with claim 13 in the form of a tablet, capsule, solution or suspension.

15. A method of treating a bacterial infection in a meal in need of such treatment comprising administering to said mammal a compound of claim 1 in an mount effective to treat said bacterial infection.

16. A method of treating a bacterial infection in accordance with claim 15 wherein the compound is administered orally.

17. A pharmaceutical composition comprising a compound of claim 1 and a DHP inhibitor in combination with a pharmaceutically acceptable carrier.

18. A pharmaceutical composition according to claim 17 wherein the DHP inhibitor is 7-(L-2-amino-2-carboxyethylthio)-2-(2,2-dimethylcyclopropanecarboxamide)-2-heptenoic acid.

19. A method of treating a bacterial infection in a mammalian subject in need of such treatment, comprising administering to such subject an antibacterially effective amount of a compound of claim 1 and an inhibitorily effective amount of a DHP inhibitor.

20. The method according to claim 19, wherein the DHP inhibitor is 7-(L-2-amino-2-carboxyethyl-thio)-2-(2,2-dimethylcyclopropanecarboxamide)-2-heptenoic acid.

* * * * *